United States Patent [19]
Rozengurt et al.

[11] Patent Number: 5,434,132
[45] Date of Patent: Jul. 18, 1995

[54] NEUROPEPTIDE ANTAGONISTS

[75] Inventors: Enrique Rozengurt; Penella Woll, both of London, England

[73] Assignee: Imperial Cancer Research Technology, Ltd., London, England

[21] Appl. No.: 147,896

[22] Filed: Nov. 2, 1993

Related U.S. Application Data

[63] Continuation of Ser. No. 994,443, Dec. 23, 1992, which is a continuation of Ser. No. 573,158, filed as PCT/GB89/00300, Mar. 21, 1989, abandoned.

[30] Foreign Application Priority Data

Mar. 21, 1988 [GB] United Kingdom .................. 880664

[51] Int. Cl.$^6$ ..................... A61K 38/08; A61K 38/11; A61K 38/16; C07K 11/00
[52] U.S. Cl. ........................ 514/2; 530/329; 530/314; 530/315
[58] Field of Search ............... 424/198.1; 530/326, 530/327, 328, 329; 514/2, 314, 315

[56] References Cited

FOREIGN PATENT DOCUMENTS

WO88/07551 10/1988 WIPO .

OTHER PUBLICATIONS

Dermer (1994) Bio/Technology 12:320.
Zachary et al (1987) J Biol Chem 262(9) 3947–3950.
Reiser et al (1988) Eur J Pharmacol 145:273–280.
Woll et al (1988) PNAS 85:1859–1863.
Kris et al., J. Biol. Chem. (1987) 262(23):11215–11220.
Brown et al., Chem. Abstracts (1988) 109(1):111–112.
Fischer et al., J. Biol. Chem. (1988) 263(6):2808–2816.
Sundan, Biol. Abstracts/RRM (No. 35054560).
Sinnet-Smith et al., Chem. Abstracts (1989) 110(11):124.

*Primary Examiner*—Christine M. Nucker
*Assistant Examiner*—M. P. Woodward
*Attorney, Agent, or Firm*—Morrison & Foerster

[57] ABSTRACT

Oligopeptides have been found that antagonist cell proliferation stimulated not only by bombesin-like peptides but also other neuropeptides e.g. vasopressin and bradykinin. These oligopeptides block a broad family of mitogenic neuropeptides that bind to receptors that use the inositol signalling pathway and one such receptor has been identified. These oligopeptides are of particular interest in relation to small cell lung cancer.

1 Claim, 13 Drawing Sheets

NEUROPEPTIDE ANTAGONISTS

This application is a continuation, of application Ser. No. 07/994,44.3 , filed Dec. 23, 1992, which is a continuation of 07/573,158, filed as PCT/GB89/00300, Mar. 21, 1989 (now abandoned).

This invention relates to antagonists to various receptors for neuropeptides, in particular to antagonists that are non-structural analogues of the specific mitogenic neuropeptide ligand. Neuropeptides are increasingly implicated in the control of cell proliferation[1]. The amphibian tetradecapeptide bombesin and its mammalian homologue, gastrin-releasing peptide (GRP) are potent mitogens for mouse fibroblasts and may act as autocrine growth factors for small cell lung cancer[3].

In our International Patent Application WO88/07551 we describe certain new peptides that are receptors for cectain peptides of the bombesin family. We also describe antagonists to the bombesin receptors including two known compounds that we have found to be particularly valuable as bombesin receptor antagonists. These antagonists are analogues of an 11-mer neuropeptide called substance P which is of interest in studies in pain transmission. Substance P has the formula:

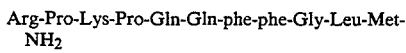
Arg-Pro-Lys-Pro-Gln-Gln-phe-phe-Gly-Leu-Met-NH$_2$

A commercially available analogue of Substance P, that we call antagonist A, has the formula:

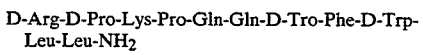
D-Arg-D-Pro-Lys-Pro-Gln-Gln-D-Tro-Phe-D-Trp-Leu-Leu-NH$_2$

A further commercially available structural variant of substance P which we have disclosed in our above-mentioned Patent Application is antagonist D which has the formula:

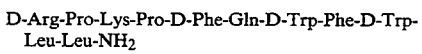
D-Arg-Pro-Lys-Pro-D-Phe-Gln-D-Trp-Phe-D-Trp-Leu-Leu-NH$_2$

In our above-mentioned Patent Application, we have described how our work with antagonist A and antagonist D has drawn to our attention the importance of position 5 in the amino acid sequence of antagonist A and antagonist D and we have referred to valuable further antagonists which are amino acid position 5 variants of antagonist A arid antagonist D where position 5 contains a D-Trp, D-Tyr or Me-Phe group.

In the work described in our above-mentioned Patent Application, we suggested that the various antagonists that we have described acted as antagonists by binding the ligand binding site on the receetor and that by so doing, the compounds were of medical interest in that they would be able to influence cell proliferation that occurred under the influence of the neuropeptide/receetor interactions.

Our further research work has led us to the conclusion that while the various antagonists that we have described in our above-mentioned Patent Application do bind to the receptor, and hence are of medical interest for the reason mentioned, the binding is not at the ligand binding site but is at a different binding site on the receptor. We reached this conclusion from our further researches that indicate that our antagonists will bind not only with the bombesin receptors of the tyoe described in our above-mentioned Patent Application but also with other neuropeptide receptors that, in common with the bombesin receptor, use the inositol signalling pathway. There are at least two further such receptors, the bradykinin receptor and the vasopressin receptor and antagonists A and D have been found capable of binding with these receptors. This particular property of antagonists A and D is in comolete contrast to the properties of bombesin itself which, by definition will bind to the bombesin receptors but will not bind to the vasopressin or bradykinin receptors. This shows that the binding site of antagonist A and D on the bombesin receptor is not the ligand binding site but is in fact probably a separate conserved domain which is also to be found in the other receptors using the inositol signalling pathway.

Our most recent discovery therefore increases the medical importance of antagonists A and D and analogues thereof in that they are able to influence not only cell proliferation occurring under the influence of bombesin-like peptides but cell prolificration occurring under the influence of a much wider range of mitogenic neuropeptides.

Accordingly, the present invention provides antagonist A, antagonist D and analogues thereof for use in a method of influencing cell proliferation that is influenced by neuropeptides that normally bind to receptors that use the inositol signalling pathway.

By analogues of antagonist A and antagonist D we mean oligopeptides of 6 to 11 amino acids having hornology at at least positions 7, 9 and 10 of the antagonist A molecule, which is a substance P antagonist and all of which additionally bind to the bombesin/GRP, bradykinin and vasopressin receptors. One such analogue of particular interest is antagonist G of formula:

Arg.D-Trp.MePhe.D-Trp-Leu-Met-NH$_2$.

In addition to the antagonists the present invention extends to conserved domains which are shared by neuropeptide receptors which use the inositol signalling pathway to stimulate growth and which domains have the following characteristic properties:

a) The domains are present in neuropeotide receetor molecules which use the inositol signalling pathway (e.g. bombesin/GRP, vasooressin, bradykinin;

b) antagonists A, D and G will each bind to such domains and inhibit the effects of multiple specific neuropeptide ligands (as described in a)) to which the receptor specifically responds;

c) When acting on such domains antagonist D is consistently 5–10 fold more potent in its inhibition than antagonist A;

d) The specificity of binding of the conserved domains as described in a) is distinct from the specificity of binding of the ligand receptor itself;

e) Antagonists that react with the conserved domains described in a) are not structural variants of the specific ligand.

In the individual case of the bombesin/GRP receptor described in our above-mentioned Patent Application, the conserved domain is part of a molecule having the following physical properties in oreparations made from intact cells:

1. It is a single chain glycopolypeptide, rich in mannose side chains.

2. It will bind selectively with polyoeotides of the bombesin type.

3. It has a molecular weight of 75 to 85 Kilodaltons (Kd).

4. It has an isoelectric point of 6.4 to 6.9.

5. Its core protein, obtained using endo-beta-Nglucosaminidase from Flavobacter ium meningoseoticum, has a molecular weight of about 42Kd.

In our above-mentioned Patent Application, we describe the isolation from intact Swiss 3T3 cells of the bombesin receptor molecule to which antagonists A and D also bind. The receptor is isolated from a homogenate of the 3T3 cells. We have now found that the oresence of $Mg^{++}$ions during cell homogenisation is important for isolatina from membrane preparations a receptor having binding activity for at least gastrin releasing peptide (GRP), the mammalian homologue of bombesin. The binding of GRP to the receptor produced from 3T3 cells in the presence of $Mg^{++}$is reversible, the equilibrium dissociation constant Kd calculated by kinetic analysis being $1,9 \times 19^{10}M$. The binding of GRP was also found to be saturable, Scatchard analysis (equilibrium binding) indicated a single class of high affinity sites having a Kd of $2.1 \times 10^{-10}M$ at 15° C. These Kd values further characterize the polypeptide containing the conserved domains of the invention.

In addition, the present invention provides all antagonists that are non-structural analogues of mitogenic neuropeptides that react via the conserved domains described above with multiple neuropeptide receptors that use the inositol signalling pathway (e.g. bombesin, vasopressin, bradykinin).

The present invention also includes antibodies, particularly monoclonal antibodies, to the putative conserved domains of the neuropeptide receptors of the invention. Such antibodies can be obtained by injecting an immunogen in a host animal from which one may recover serum containing antibodies or antibody producing cells which can be immortalised and give rise to cells producing monoclonal antibodies. The immunogen can be the conserved domain polyoeptide of the invention and, in particular, can be the conserved domain polypeptide obtained from membrane preparations of Swiss 3T3 cells homogenised in the presence of $Mg^{++}$. The antibodies of the invention are useful in relation to diagnosis or theraoy of cancers or other diseases associated with disorders of neuropeptides that use the inositol signalling pathway. When used as diagnostics, the antibodies may carry a revealing label, e.g. radio-active, enzyme, fluorescent etc., and/or can be immobilised on a solid support. Diagnostic test kits may include, as one component, a purified conserved domain or antibody of the invention. When used as therapeutic agents, the antibodies of the invention may be conjugated to cytotoxic entities.

Additionally, the antagonists, particularly antagonist A or D or G, are of interest in the retarding or abolition of the growth of small cell lung cancer and, when labelled, in the diagnosis, in vitro or in vivo of small cell lung cancer. Such labelling may be direct on the antagonist molecule, or indirect through a molecule that binds to the antagonist.

The conserved domains or antibodies of the invention may be formulated with conventional parenteral carriers so that they can be administered parenterally when linked to labels or cytotoxic moieties where they are of interest in the diagnosis or therapy of cancers or other diseases associated with disorders of neuropeptides that use the inositol signalling pathway.

Included within the scope of this invention are antagonists A, D and G for use in the production of a medicament for influencing cell proliferation influenced by neuropeptides that normally bind to receptors that use the inositol signalling pathway and particularly antagonist G for use in the production of a med icament for the treatment of or diagnosis of small cell lung cancer. For this purpose antagonist A or D or G can be administered parenterally in an effective dose to a host in need of such treatment or diagnosis.

The following Examples are given to illustrate the invention.

EXAMPLE 1

Swiss 3T3 cells are widely available for experimental use and are available from the American Type Culture Collection in Rockville, Md., U.S.A., under the Deposit No. ATCC-CCL92.

Figure 1A:
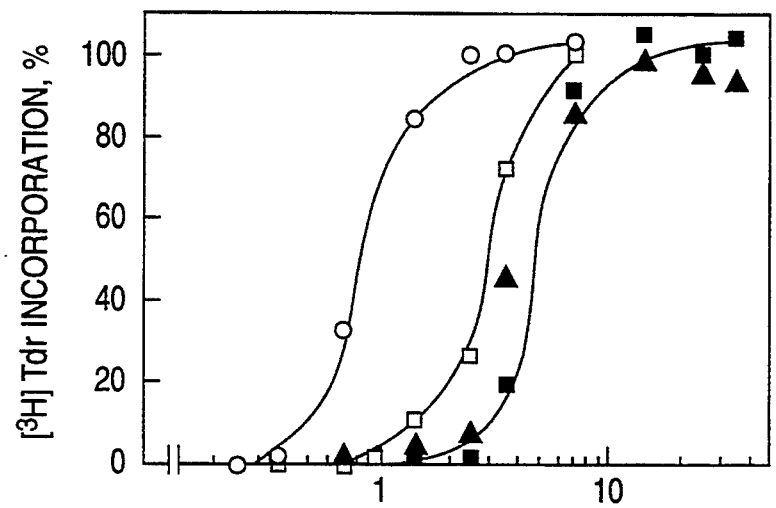
FIGS. 1 and 2 illustrate results of experiments described in Example 1.
Figure 1B:
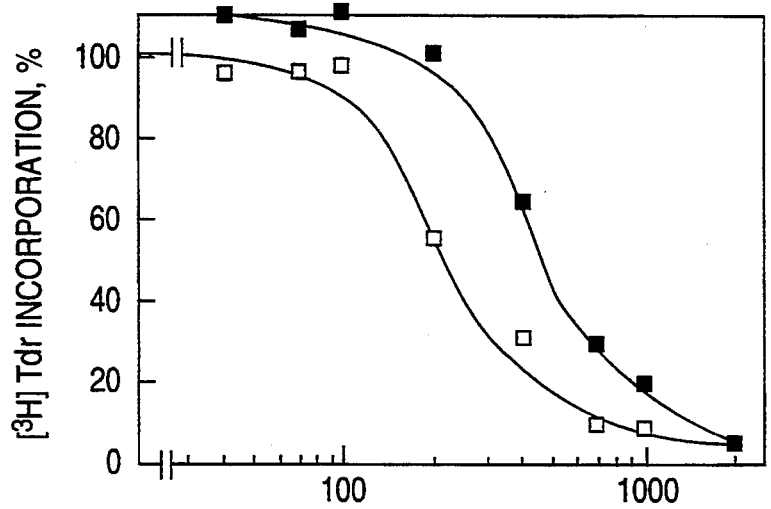
Figure 1C:
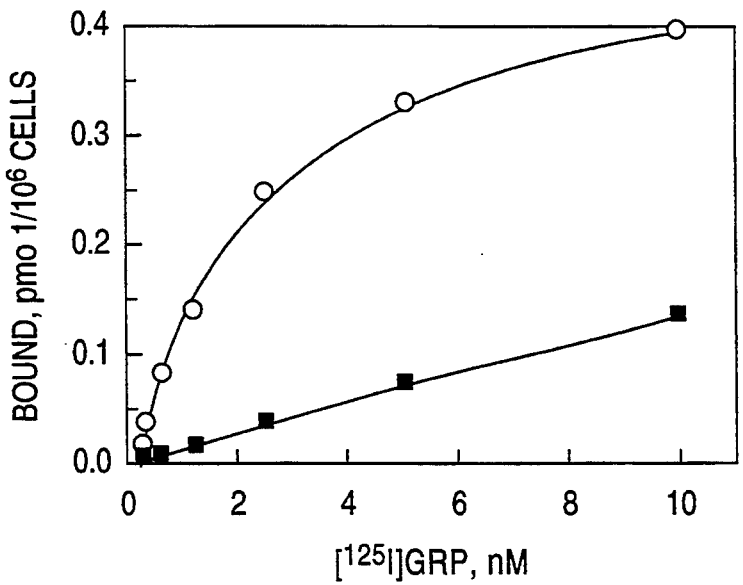
Figure 1D:
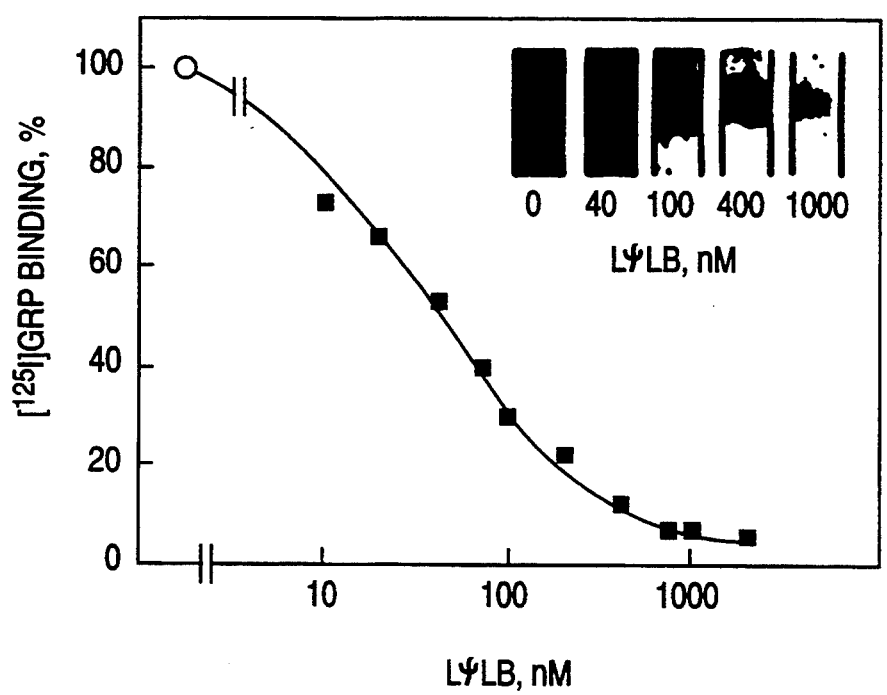

The pseudopeptide [Leu13-ΨJ(CH$_2$NH)Leu$^{14}$] bombesin was synthesised during a systematic study of peptide backbone modifications in bombesin analogues[5]. It was shown to cause 50% inhibition (IC$_{50}$) of bombesin-stimulated amylase release from guinea pig pancreatic acini at 35 nM. We have now characterised its mode of action in Swiss 3T3 cells. DNA synthesis, measured by [$^3$H]thymidine incorporation into quiescent cells[6] in the presence of insulin 1 μg/ml and varying concentrations of GRP was strongly inhibited by [Leu$^{13}$ Ψ(CH$_2$NH)Leu$^{14}$-bombesin with an effect at 1 μM equivalent to that of 20 uM [DArg$^1$, DPhe$^5$, DTrp7,9, Leu$^{11}$]substance P i.e. Substance D (FIG. 1A). The IC$_{50}$ for [Leu13-Ψ(CH$_2$NH)Leu$^{14}$]bombesin was 455 nM in the presence of 3.6 nM GRP (FIG. 1B). In addition [Leu$^{13}$-Ψ(CH$_2$NH)Leu$^{14}$] bombesin blocked the earliest cellular events elicited by GRP[7], including Ca$^{2+}$mobilisation (5 secs) and epidermal growth factor (EGF) receptor transmodulation (1 rain), which is deoendent on protein kinas. C activation. [Leu$^{13}$-Ψ(CH$_2$NH)Leu$^{14}$]bombesin inhibited the specific binding of [$^{125}$I]GRP to the cells (FIG. 1C and D) and blocked cross-linking of [$^{125}$I]GRP to the Mr 75,000-85,000 glycoprotein comooent oF the receptor (FIG. 1D, inset)[8,9]. Thus, [Leu$^{13}$Ψ(CH$_2$NH)-Leu$^{14}$]bombesin is a potent bombesin antagonist in Swiss 3T3 cells, acting at receptor level.

Figure 2A:
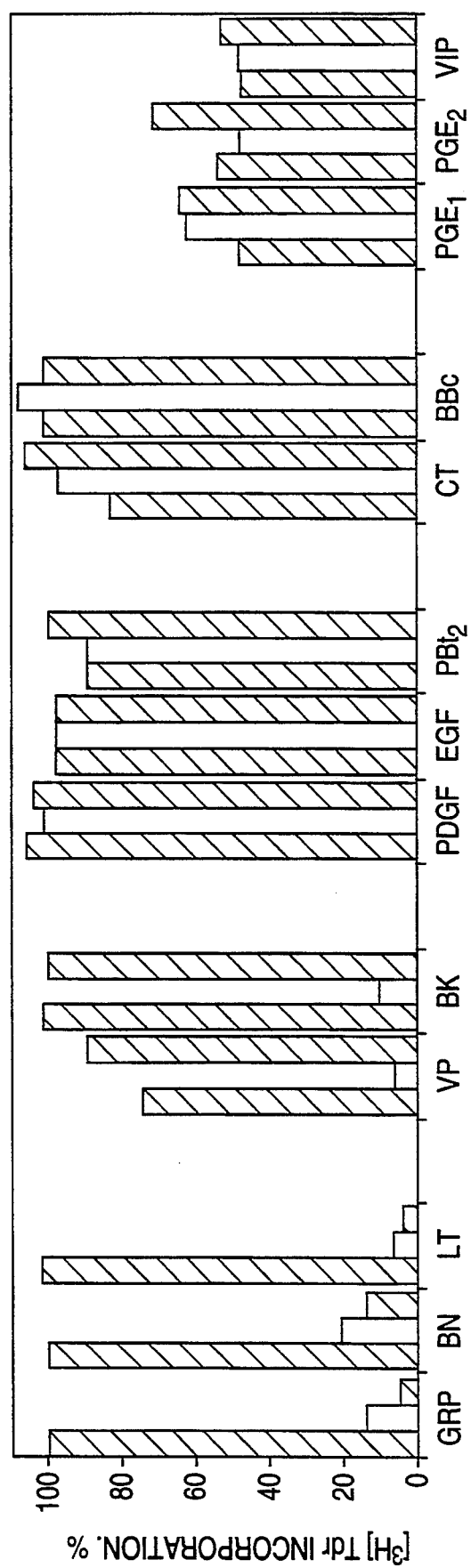
Figure 2B:
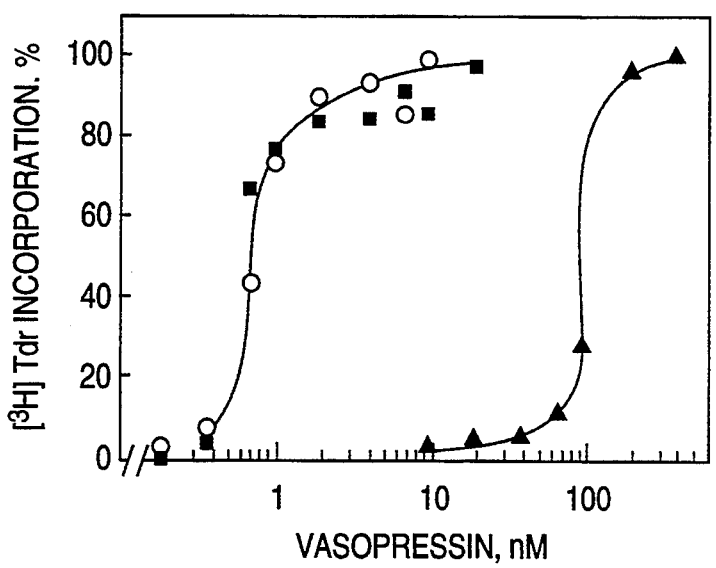

The tachykinin substance P has minimal amine acid sequence hemology with bombesin and neither inhibits the binding of [$^{125}$I]GRP nor stimulates DNA synthesis in Swiss 3T3 cells[2,10]. Our earlier-mentioned Patent Application and references 10, 11 describe how antagonist A is a bombesin antagonist and that antagonist D is 5-10 fold more potent than antagonist A. Both also inhibit vasopressin-stimulated DNA synthesis and [$^3$H]vasopressin binding in Swiss 3T3 cells 4,12,13. Because of this, we have tested the new bombesin antagonists rigorously to establish their specificity against mitogens acting through different signal transduction pathways (FIG. 2A). As expected, antagonist D and [Leu$^{13}$-$\Psi$(CH$_2$NH)Leu$^{14}$]-bombesin were both effective against various bombesin-like peptides. Neither of them inhibited mitogenesis stimulated by the polypeptide growth factors EGF and platelet-derived growth factor (PDGF), the protein kinase C activator phorbol dibutyrate, or the cAMP elevators cholera toxin and 8-bromo-cAMP. Although antagonist D was a potent inhibitor of vasopressin-induced DNA synthesis, Leu$^{13}$-$\Psi$(CH$_2$NH)Leu$^{14}$]bombesin had no effect at concentrations that strongly inhibited GRP-induced mitogenesis (FIG. 2B). This dramatic difference in specificity prompted us to compare the effects of antagonist D and [Leu$^{13}$-$\Psi$(CH$_2$NH)Leu$^{14}$]bombesin in other mitogenic neuropeptides.

Figure 2C:
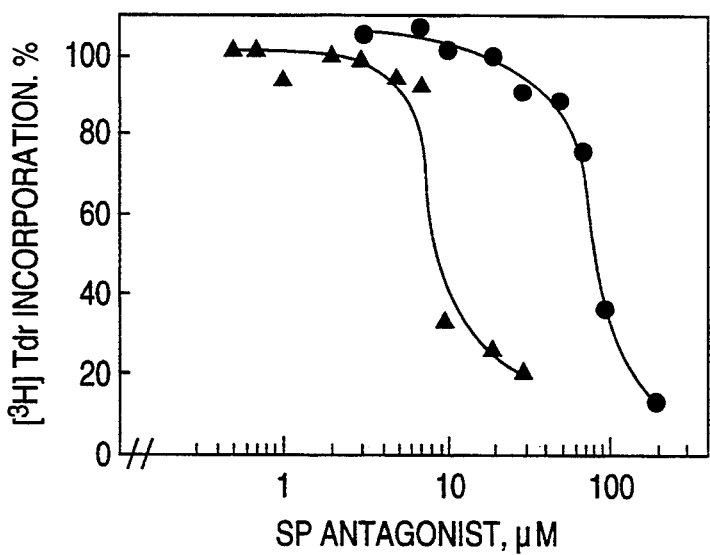
Figure 2D:
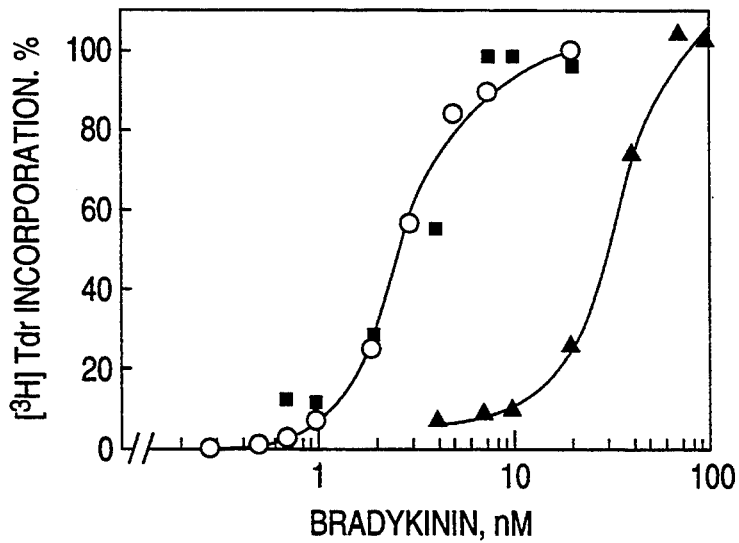

Bradykinin, like bombesin and vasopressin, stimulates calcium mobilisation and inositol phosphate turnover in several cell types[14-17]. We found that in Swiss 3T3 cells loaded with the fluorescent Ca$^{2+}$indicator Fura-2, the addition of bradykinin caused a rapid and transient increase in the cytosolic Ca$^{2+}$concentration with kinetics similar to those obtained with bombesin and vasopressin but distinct from those of PDGF[18]. Bradykinin did not inhibit the binding of either [$^3$H]vasopressin or [$^{125}$I]GRP to Swiss 3T3 cells, indicating that their receptors are distinct. In the presence off insulin, bradykinin caused maximal stimulation of DNA synthesis in these cells (FIGS. 2C & D) in contrast to its weak mitogenic effect in human fibroblasts[19,20]. Thus, bradykinin orovided a novel mitogen with which to test the new antagonists. Mitogenesis induced by 9.4 nM bradykinin was inhibited by antagonist A and antagonist D (FIGS. 2C & D) with IC$_{50}$ of 90 μM and 8.3 μM respectively which is the same relative potency obtained with GRP$^4$ and vasopressin (data not shown). Remarkably [Leu$^{13}$-$\Psi$(CH$_2$NH)Leu$^{14}$]-bombesin had no effect on bradykinin-stimulated DNA synthesis (FIG. 2C). While bombesin, bradykinin and vasopressin activate the inositol phosphate signalling pathway, vasoactive intestinal peptide (VIP) is a neuropeptide that stimulates DNA synthesis via cAMP[21]. Neither antagonist D nor [Leu$^{13}$-$\Psi$(CH$_2$NH)Leu$^{14}$]bombesin inhibited mitogenesis stimulated by VIP (FIG. 2A).

The striking difference in specificity between [Leu$^{13}$-$\Psi$(CH$_2$NH)Leu$^{14}$]bombesin and the substance P antagonists presented here has important implications. The substance P antagonists block the mitogenic responses elicited through three distinct receptors, bombesin/GRP, bradykinin and vasopressin. They do not block those elicited by other mitogens which act through different transmembrane signalling pathways including cAMP and protein kinase C activation. The substitution of the two amino acids distinguishing antagonist D from antagonist A causes a consistent 5-10 fold increase in potencV against each mitogen, which suggests that these antagonists recognise a common site in their distinct receptors. As bombesin, bradykinin, vasopressin and the substance P antagonists are structurally unrelated this putative binding site cannot be the ligand recognition site. Thus, we believe that antagonist D and antagonist A recognise a conserved domain on each of the receptors. Since a common function of these receptors is the induction of inositol polyphosphate formation and Ca$^{2+}$mobilisation, we believe that the substance P antagonists could bind with a region on each receptoc that is essential for coupling with G oroteins involved in Ca$^{2+}$signalling$^{22}$. Our theories require that an antagonist structurally related to one of these mitogens should bind to its discrete ligand-recognition site causing specific inhibition of its biological effects but not those of the other mitogenic neuropeptides. Our results demonstrate that the pseudopeptide antagonist [Leu$^{13}$-$\Psi$(CH$_2$NH)Leu$^{14}$]bombesin satisfies these criteria.

EXAMPLE 2

The ability of antagonists A, D and G to inhibit the growth in vitro of a small cell lung cancer (SCLC) cell line was tested. The cell lines used were a) H69 and H128 from the ATCC in Maryland USA;

b) H209, H345 and H510A obtained from Dr. A. Gazdar at NCI, NIH, Maryland USA;

c) UCH25 from Dr. P. Beverley, University College, London, England.

Antagonist A when tested was found effective in inhibiting growth of SCLC at concentrations of 50-150 μM in 5 of 5 cell lines tested: H69, H82, H128, H417 and UCH25.

Figure 3:
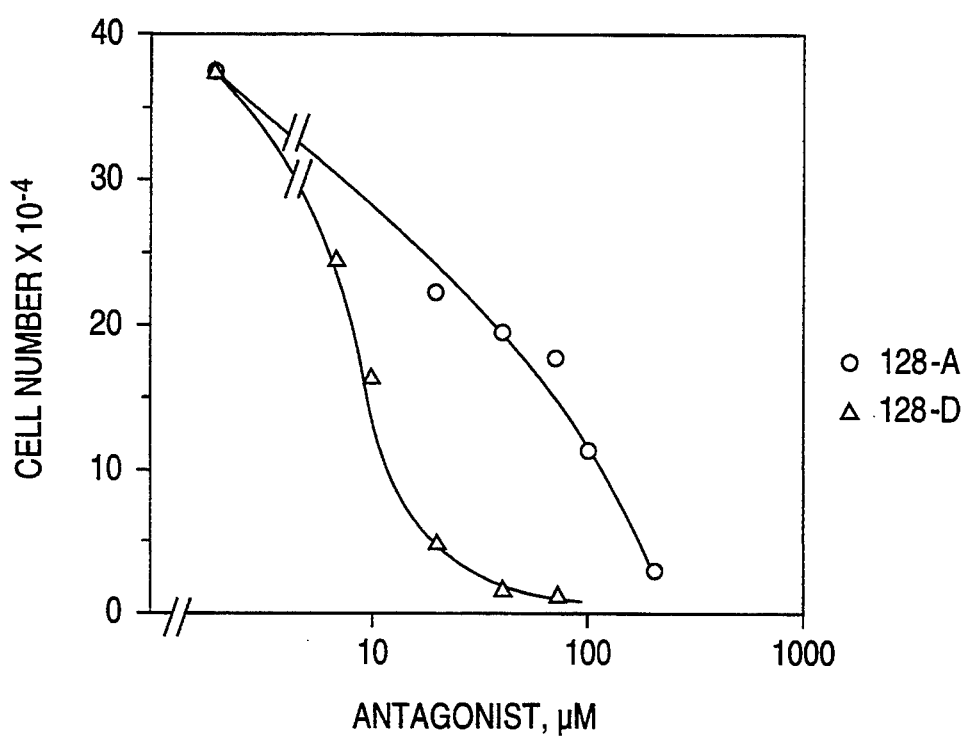
FIGS. 3 to 5 illustrate the results of the inhibitory effect of antagonists A, D and G on small cell lung cancer cell lines as described in Example 2.
Figure 4:
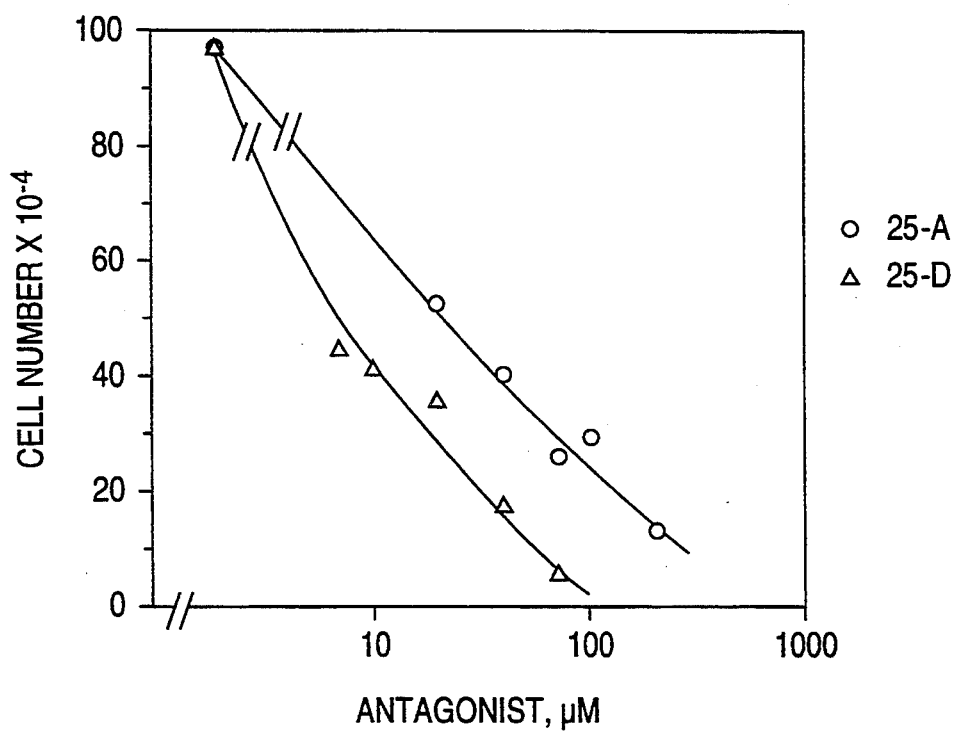

Antagonist D was found to be consistently 5-10 fold more potent than Antagonist A in inhibiting growth of SCLC, see FIGS. 3 and 4. Antagonist D abolishes cell growth at 40-50 μM and is active in 6 of 6 cell lines tested: H69, H128, H209, H345, H510A and UCH25.

Figure 5:
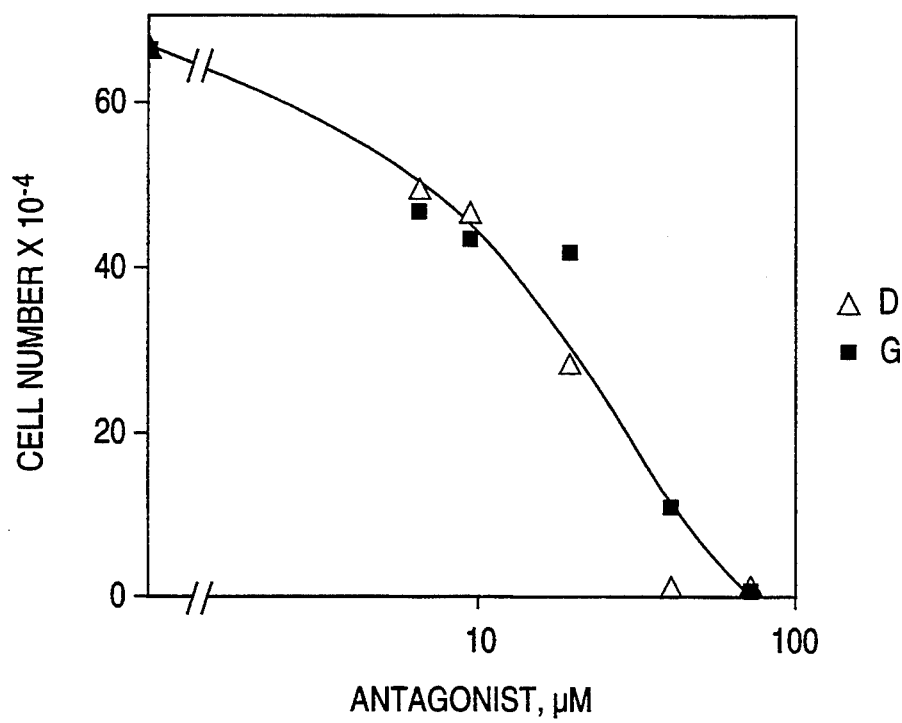

Antagonist G was found to be as potent as Antagonist D as an antagonist of vasopressin induced cell growth in Swiss 3T3 cells, but less potent as an antagonist of growth induced by either bradykinin or GRP. In SCLC cells antagonist G is equipotent with antagonist D in terms of inhibition of growth, see FIG. 5. This activity has been demonstrated in 4 of 4 cell lines tested: H69, H209, H345 and H510A.

In calcium mobilisation tests, transient elevation of intracellular [Ca 2+] has been demonstrated in several SCLC cell lines in response to bradykinin, GRP and vasopressin. These responses can be blocked by 20 μM antagonist D in 3 of 3 lines tested (H69, H345, H510A) and by 20 μM antagonist G in H510A.

REFERENCES

1. Zachary, I., Woll, P.J. & Rozengurt, E. Devel. Biol. 124, 295-308 (1987).

2. Rozengurt, E. & Sinnett-Smith, J. Proc. natn. Acad. Sci. USA. 80, 2936-2940 (1983).

3. Cuttitta, F. et al. Nature 316, 823-826. (1985)

4. Woll, P.J. & Rozengurt, E. Proc. natn. Acad. Sci. USA. in press.

5. Coy, D.H. et al. J. Biol. Chem. 263, 5056-5060 (1988)

6. Dicker, P. & Rozengurt, E. Nature 287, 607-612 (1980).

7. Rozengurt, E. Science 234, 161-166 (1986).

8. Zachary, I. & Rozengurt, E. J. Biol. Chem. 262, 3947-3950 (1987).

9. Sinnett-Smith, J., Zachary, I. & Rozengurt, E. J. Cell. Biochem. 38, 237-249 (1988)

10. Zachary, I. & Rozengurt, E. Proc. hath. Acad. Sci. USA. 82, 7616-7620 (1985).

11. Jensen, R.T., Jones, S.V., Folkera, K. & Gardner, J.D. Nature 309, 61-63 (1984).

12. Corps, A.N., Rees, L.H. & Brovn, K.D. Biochem. J. 231, 781-784 (1985).

13. Zachary, I. & Rozengurt, E. Blochem. Biophys. Res. Commun. 137, 135-141 (1986).

14. Burch, R.M. & Axelrod, J. Proc. hath. Acad. Sci. USA. 84, 6374-6378 (1987).

15. Jackson, T.R., Ballam, T.J., Downes, C.P. & Banlay, M.R. EMBO J. 6, 49–54 (1987).

16. Osugi, T., Imaizumi, T., Mizushima, A., Uchida, S. & Yoshida, H. J. Pharmacol. Exp. Ther. 240, 617–622 (1987).

17. Tilly, B.C. et al. Blochem. J. 244. 129–135 (1987).

18. Lopez-Rivas, A., Mendoza, S.A., Nanberg. E., Sinnett-Smith, J., & Rozengurt, E. Proc. hath. Acad. Sci. USA. 84, 5768–5772 (1987).

19. Oven, N.M. & Villereal, M.L. Cell 32, 979–985 (1983).

20. Coughlin, S.R., Lee, W.M.F., Williams, P.W., Giels, G.M. and Williams, L.T. Cell 43, 243–251 (1985).

21. Zurier, R.B., Kozma, M., Sinnett-Smith, J. & Rozengurt, E. Exp. Cell Res. in press.

22. Stryer, L. & Bourne, H.R. Ann. Rev. Cell Biol. 2, 391–419 (1986).

Figure Legends

FIG. 1: Effects of [Leu$^{13}$-$\Psi$(CH$_2$NH)Leu$^{14}$bombesin (L$\Psi$LB) in murine Swiss 3T3 cells. A. Dose-response curves for GRP-induced DNA synthesis with 1 $\mu$Ci/ml (1 $\mu$m) [$^3$H]thymidine ([$^3$H]Tdr) and 1 $\mu$g/ml insulin alone (o) or with 500 mM (□) or 1 $\mu$M (■) L$\Psi$LB, or 20 $\mu$M Antagonist D (□). Values are expressed as a percentage of [$^3$H]Tdr incorporation obtained with 10% fetal calf serum. B. Dose-response curves for L$\Psi$LB inhibition of DNA synthesis induced by 2.4 nM (□) and 3.6 nM (■) GRP with 1 $\mu$g/ml insulin and 1 $\mu$Ci/ml [$^3$H]Tdr. C. Concentration-dependence of [$^{125}$I]GPR binding to Swiss 3T3 cells at 37° C. Specific cell-associated binding is shown in the absence (o) or presence (■) or 500 nM L$\Psi$LB. D. Inhibition of specific [$^{125}$I]GRP binding to Swiss 3T3 cells by L$\Psi$LB (■) expressed as a percentage of binding obtained with 1 nM [$^{125}$I]GRP in the absence of antagonist (o). Inset. Effect of LwLB on the affinity-labelling of the Mr 75–85000 bombesin receptor-associated protein.

Methods: Swiss 3T3 cells were maintained in culture and assays of DNA synthesis performed as previously described 2,4,6 In all the figures, values shown represent the mean of at least 2 determinations. For [$^{125}$I]GRP binding studies, confluent and quiescent cells were washed twice with Dulbecco's modified Eagle's medium then incubated at 37° C. in 0.75 ml of binding medium$^{10}$ containing the stated concentration of [$^{125}$I]GRP and L$\Psi$LB. Cell-associated [$^{125}$I]GRP binding was measured after 30 rains. Non-specific binding was determined by the addition of 500-fold excess of unlabelled GRP. For crosslinking studies, confluent and quiescent cells were washed twice with binding medium$^8$ then incubated at 24° C. in 1 ml of binding medium (pH 7.0) containing 1 nM [$^{125}$I]GRP and various concentrations of L$\Psi$LB. After 10 mins they were washed twice with binding medium, then incubated at 24° C. in 1 ml containing 6ram ethylene glycol bis(succinimidylsuccinate) at pH 7.4. After 10 mins they were washed twice with cold binding medium and solubilised in 100 $\mu$l sample buffer$^8$, then immediately boiled for 5 mins, and electrophoresed on a 10% polyacrylamide gel.

FIG. 2. Specificity of the bombesin antagonists. A. DNA synthesis with a variety of mitogens measured (as in FIG. 1) in the presence of 1 $\mu$Ci/ml [$^3$HTdr] and 1 $\mu$g/ml insulin alone (■) or with 20 $\mu$M antagonist D or 1 $\mu$m L$\Psi$LB (□). Mitogens were used at the following concentrations: GRP, 3.6 nM; bombesin (BN), 1.2 nM; litorin (LT), 1.8 nM, vasopressin (VP), 9.2 nM; bradykinin (BK), 9.4 nM; PDGF, 1 nM; EGF, 0.4nM; Phorbol 12,13-dibutyrate (PBt$_2$), 50 ng/ml; cholera toxin (CT), 100 ng/ml with isobutylmethylxanthine (IBMX), 10 $\mu$M; 8-bromo-cAMP (8Bc), 2.5 mM; prostaglandin E$_1$ (pGE$_1$), 100 ng/ml with IBMX, 10 $\mu$M; prostaglandin E$_2$(PGE$_2$), 200 ng/ml with IBMX, 10 $\mu$M; VIP, 3.0 nM with4- (3-butoxy-4-methoxybenzyl) -2-imidozolidine, 5 $\mu$M. Values are expressed as a percentage of [$^3$H]Tdr incorporation obtained with 10% fetal calf serum.

B. Dose-response curves for vasopressin-induced DNA synthesis with 1 $\mu$Ci/ml [$^3$H]Tdr and 1 $\mu$g/ml insulin alone (o) or with 1 uM L$\Psi$LB (■) or 20 pM antagonist D (□). C. Inhibition of DNA synthesis stimulated by 9.4 nM bradykinin with 1 $\mu$Ci/ml [$^3$H]Tdr and 1 $\mu$g/ml insulin, by various concentrations of antagonist D ($\Delta$) or Antagonist A (o). D. Dose-response curves for bradykinin-induced DNA synthesis with 1 $\mu$C/ml [$^3$H]Tdr and 1$\mu$g/ml insulin alone(o) or with 1 $\mu$M L$\Psi$LB (■) or 20 $\mu$M antagonist D ($\Delta$).

EXAMPLE 3

The purpose of the present experiment was to examine the binding of $^{125}$I-GRP to membrane preparations derived from Swiss 3T3 cells in order to determine the kinetic and equilibrium characteristics of the binding reaction in the absence of receptor internalization and ligand degradation. In the course of these studies ve found that the presence of Mg$^{2+}$ during cellular homogenization and binding assay vas crucial to preserve $^{125}$I-GRP binding activity in the resulting membrane preparation. Exploiting this observation, we now demonstrate that binding of $^{125}$I-GRP is specific, rapid, reversible, saturable and displaced by a variety-of non-radioactive agonists and antagonists in a concentration-dependent manner. We also report that the homobifunctional cross-linking agent EGS covalently linked $^{125}$I-GRP to a single Mr 75000–85000 protein in S2iss 3T3 membranes prepared in the presence of Mg$^{2+}$. The findings indicate that this protein is the receptor or a binding subunit of the mitogenic bombesin receptor.

EXPERIMENTAL PROCEDURES

Materials: Bombesin, GRP, litorin, vasopressin, bradykinin, somatostatin, substance K, substance P, vasoactive intestinal peptide (VIP), epidermal growth factor (EGF), insulin, phorbol 12,13 dibutyrate (PBt$_2$), bovine serum albumin (BSA), aprotonin, bacitracin, soybean trypsin inhibitor, phenylmethylsulphonyl fluoride and polyethylenimine were purchased from Sigma. GRP(1–16), bombesin (8–14), neuromedin B, [DArg$^1$,DPro$^2$,DTrp$^{7,9}$,Leu$^{11}$]substance P and [DArg$^1$,DPhe$^5$,DTrp$^{7,9}$,Leu$^{11}$]substance P were from Bachem Fine Chemicals. Ethyleneglycolbis(succimidylsuccinate) (EGS), and disuccinimidyl subcrate (DSS), were obtained from Pierce. Recombinant platelet derived growth factor c-sis (PDGF), recombinant fibroblast growth factor (FGF) and $^{125}$I-GRP (1800–2200 Ci/mmol) were purchased from Amersbam International. All other reagents were of the highest grade available.

Cell culture: Cultures of Swiss 3T3 cells (34) were maintained in 90 mm Nunc Petri dishes in Dulbecco's modified Eagle's medium (DMEM) containing 10% fetal bovine serum, penicillin 100 U/ml, and streptomycin (100 ug/ml) in humidified 10% CO$_2$ and 90% air at 37° C. For the preparation of membranes, 3×10$^6$ cells were subcultured into 1850 cm$^2$ Falcon roller bottles with 200 ml of the same culture medium and were grown to confluence without a change of medium for 6–7 days. The final cell density was $3 \times 10^7$ cells/flask.

Membrane preparation: Cultures in roller bottles were washed twice with 150 ml phosphate buffered saline (PBS) (0.14M NaCl, 5 mM KCl, 0.01M $Na_2HPO_4$, 1.8 mM $KH_2PO_4$; pH 7.2) at room temperature. The cells were then harvested at 4° C. by scraping into ice cold PBS containing 5 mM $MgCl_2$, 1 mM [ethylenebis(oxyethylenenitrilo)]tetraacetic acid (EGTA), 1 mg/ml bacitracin, 10 ug/ml aprotonin, 1 mg/ml soybean trypsin inhibitor and 50 $\mu$M phenylmethylsulphonyl fluoride. All subsequent steps were carried out at 4° C. The cells were pelleted by centrifugation at 750 x g for 10 minutes and resuspended $5 \times 10^6$/ml in solution A containing 50 mM 4-(2-Hydroxyethyl)-1-piperazineethanesulfonic acid (Hepes), 5 mM $MgCl_2$, 1 mM EGTA, 1 mg/ml bacitracin, 10 $\mu$g/ml aprotonin, 1 mg/ml soybean trypsin inhibitor and 50 $\mu$M phenylmethylsulfonyl fluoride, adjusted to pH 7.4 with NaOH at 4° C. Cells were then disrupted using a Dounce homogeniser (A pestle) 75 strokes. The homogenate was centrifuged at 500 x g for 10 minutes to remove nuclear material and intact cells and the supernatant was centrifuged again at 30000 x g for 30 minutes. The resulting pellet, representing a membrane-enriched preparation was resuspended at a protein concentration of 5 to 10 mg/ml in solution A and stored in liquid nitrogen. For experiments, membranes were thawed and diluted to a concentration of 1 mg/ml with solution A.

Receptor binding assay: Binding assays were carried out in a total volume of 100 ul in binding medium containing 50 mM Hepes, 5 mM $MgCl_2$, 1 mg/ml bacitracin and 1% bovine serum albumin (BSA), adjusted to pH 7.4 with NaOH, unless otherwise indicated. The assays contained 25 ug of membrane protein plus 85000–125000 cpm of $^{125}$I-GRP (0.5 nM) plus the reagents specified in the individual experiments. Nonspecific (nonsaturable) binding was determined in the presence of 1$\mu$M of either bombesin or GRP and represented 5–10% of the total binding. Non-specific binding was subtracted from the total binding to obtain specific binding. The membranes were incubated for either 10 minutes at 37° C. or 30 minutes: at 15° C. as indicated. These conditions provided equilibrium binding.

The binding reactions were terminated at the specified times by rapid filtration on GF/B glass fibre filters (Whatmann, 1.0 $\mu$m pore size). Each filter was washed five times with 5 ml of PBS containing 1% BSA at 4° C. (15 s total time) using a Millipore filtration apparatus. Before the addition of membranes the filters were soaked for 24 hours in 5% polyethylenimine at 4° C. and washed with 5 ml of PBS containing 1% BSA immediately prior to use. Identical results were obtained when the assays were terminated by centrifugation for 1 minute at 14000 rpm in a MSE microfuge at 4° C. followed by three 1.0 ml washes with PBS containing 1.0% BSA. Radioactivity was determined with a Beckmann $\gamma$-counter. The recovery of measurable binding sites in the membrane preparation expressed as a percentage of total sites determined in intact 3T3 cells was approximately 50%. The specific binding activity increased from 204±30 fmole/mg protein in the intact cells to 564±50 fmole/mg protein in the membrane preparation.

Kinetic studies: The kinetics of binding of $^{125}$I-GRP was analysed as a bimolecular reaction:

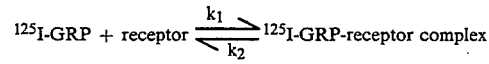

The second order rate constant of association was obtained ($k_2$) using the following equation (see ref. 35 for derivation):

$$k_1 = \left[ \frac{1}{t} \; \frac{Beq}{Beq^2 - BoLo} \right] \left[ \ln \frac{Beq - Bt}{BoLo - Beq\, Bt} + \ln \frac{BoLo}{Beq} \right] \quad (1)$$

When $\ln[(Beq - Bt)/(BoLo - Beq\, Bt)]$ is plotted as a function of time $k_1$ can be determined from the slope by the following relation $k_1$=slope x [Beg/(Beg$^2$ - BoLo)](36) where Bo and Lo are the initial concentrations of receptor and ligand respectively. Bt is the concentration of receptor-ligand complex at time t and Beq is its concentration at equilibrium. Equation (1) takes into account the decrease in free ligand concentration that occurs during the binding reaction.

The first order rate constant of dissociation was determined from the slope of the line obtained by plotting ln(Bt/Beg) as a function of time.

Chemical cross-linking of $^{125}$I-GRP to receptors: Membrane protein (150 $\mu$g) prepared from Swiss 3T3 cells as described above was incubated at 30° C. or 15° C. for 10 minutes or 30 minutes respectively in 500 $\mu$l of cross-linking medium (50 mM Hepes, 5 mM $MgCl_2$, 1 mg/ml bacitracin, pH 7.4) containing 0.5 nM $^{125}$I-GRP and any other reagents as specified in 'Results'. BSA was omitted from all solutions used in the cross-linking studies. At the end of the incubation the membranes were centrifuged at 1000 rpm for 1 minute in a MSE microfuge at room n temperature. The pellets were then resuspended in cross-linking medium containing 4 mM of the cross-linking reagent (EGS) and incubated at 37° C. or 15° C. for 5 minutes or 15 minutes respectively. The reaction was terminated by centrifugation for 1 minute followed by one wash with cross-linking medium and centrifugation. Samples were solubilised in 0.20 ml of 2X sample buffer, (0.2 M Tris-HCl pH 6.8, 10% (w/v) glycerol, 6% sodium dodecyl sulphate (SDS) (w/v), 4% $\beta$-mercaptoethanol (v/v), and 2 mM EDTA), immediately heated to 100° C. for 10 minutes and analysed by one dimensional electrophoresis.

SDS-Polyacrylaaide Gel glectrophoresis: Slab gel electrophoresis was performed using 8% acrylamide in the separating gel and 4% in the stacking gel and 0.1% SDS (37). After electrophoresis gels were stained, desrained and dried down onto paper for autoradiography with Fuji x-ray film. Dried gels were exposed for 2–4 days at −70° C. Autoradiograms were scanned using an LKB ultrascan XL densitometer; and the incorporation of radioactivity into the $M_r$ 75,000–85,000 band was quantified using the Ultroscan XL internal digital integrator.

RESULTS

Figure 6A:
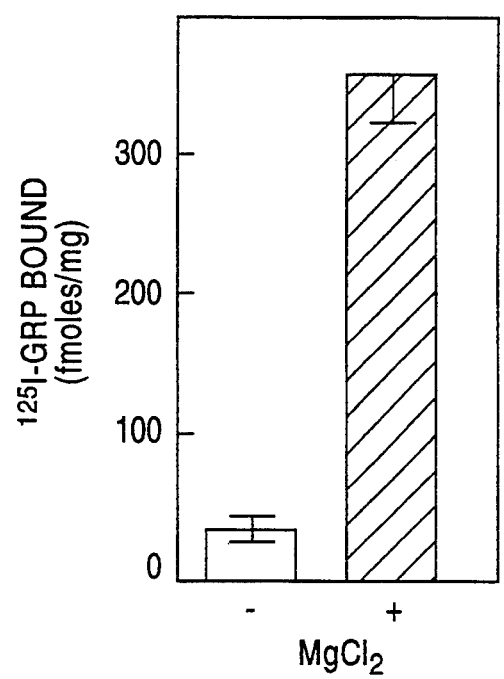
Figure 6B:
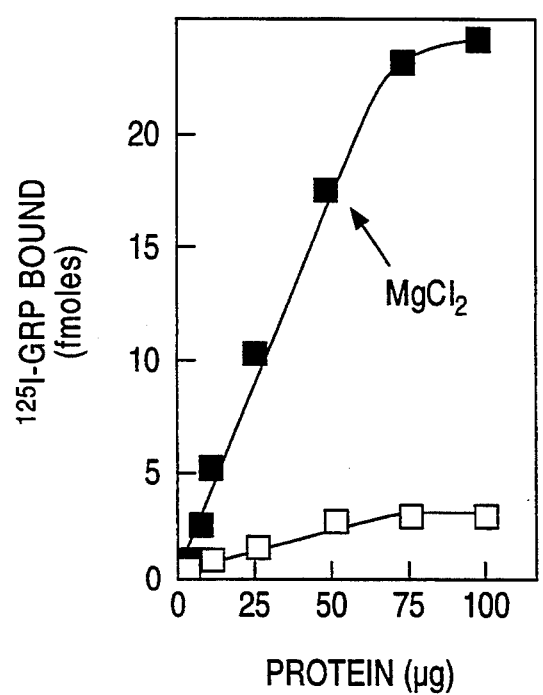
Figure 6C:
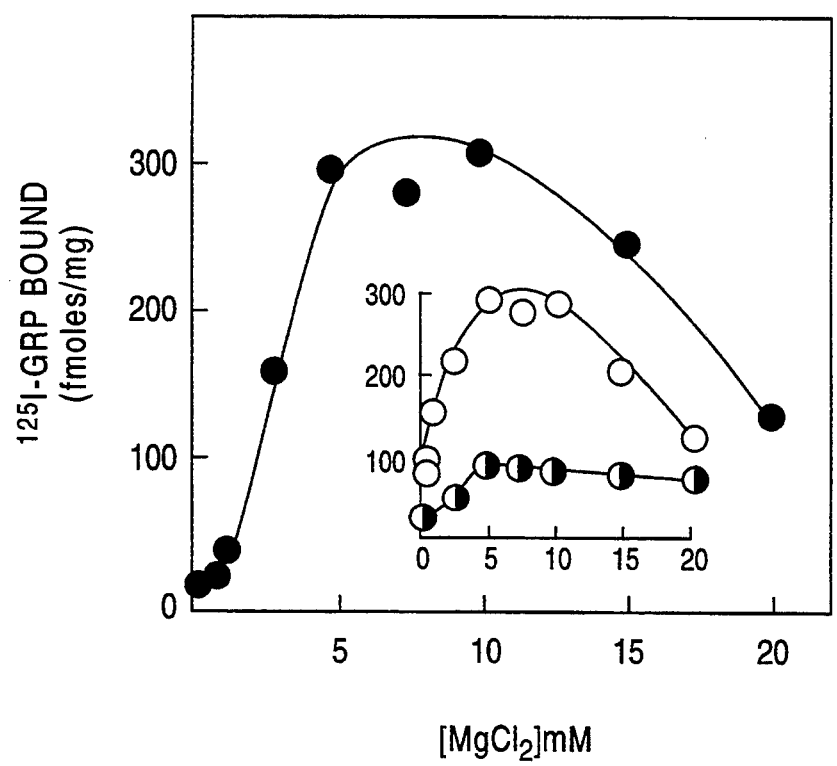

$^{125}$I-GRP binds specifically to membrane fractions of Swiss 3T3 cells: requirement of $Mg^{2+}$ Initial experiments revealed that membrane fractions of Swiss 3T3 cells prepared according to various procedures (38–43) failed to exhibit any consistent specific binding of $^{125}$I-GRP. However, we found that addition of $Mg^{2+}$ during the harvesting and homogenization of the cells as well as during the binding assay resulted in a striking increase in the specific binding of $^{125}$I-GRP to membranes (FIG. 6A). MnCl$_2$ at 2.5 mM only partially substituted for MgCl$_2$ (30% of maximum binding) whereas CaCl$_2$ had no effect. MgSO$_4$ was as effective as MgCl$_2$. Similar results were obtained when membrane binding sites were assayed by two different methods i.e. filtration and centrifugation assays. FIG. 6B shows specific $^{125}$I-GRP binding as a function of membrane concentration using the filtration assay. With membranes prepared and assayed in the presence of 5 mM Mg$^{2+}$, binding was linear up to 50 µg protein. The dependence on Mg$^{2+}$ concentration of $^{125}$I-GRP specific binding is shown in FIG. 6. Maximum binding was obtained when Mg$^{2+}$ was present at 5 mM during both the cell homogenization and binding assay (FIG. 6B). A similar dose-response relationship yes observed when the membranes were prepared in the presence of various Mg$^{2+}$ concentrations but assayed at 5 mM Mg$^{2+}$ (FIG. 6B, inset). In contrast, addition of various concentrations of Mg$^{2+}$ to the binding medium using membranes prepared in the absence of this ion increased the specific binding of $^{125}$I-GRP to only 25% of the maximum specific binding (FIG. 6B, inset). To identify the step at which Mg$^{2+}$ is necessary to preserve binding, ve added this ion at various stages of the membrane preparation. Addition of 5 mM Mg$^{2+}$ immediately after cellular homogenization or to any subsequent step failed to preserve maximum binding of $^{125}$I-GRP to membranes. This indicates that Mg$^{2+}$ is required to stabilize the binding activity during the homogenization step.

Specific binding of $^{125}$I-GRP (0.5 nM) to membrane fractions of Swiss 3T3 cells prepared in the presence of 5 mM Mg$^{2+}$ was not inhibited by other mitogens for cultured fibroblasts which are structurally unrelated to bombesin and GRP (Table 1). The neuropeptides substance P, substance K and vasoactive intestinal peptide which exhibited slight COOH-terminal homology with GRP also failed to inhibit the binding of $^{125}$I-GRP to membrane preparations. In contrast the binding was reduced markedly by addition of either unlabelled bombesin or GRP at 100 nM. These results indicate that $^{125}$I-GRP binding to membrane preparations of Swiss 3T3 cells is specific. This conclusion is reinforced by the fact that membrane fractions prepared from 3T6 cells, a cell line that neither binds $^{125}$I-GRP (8) nor responds mitogenically to this peptide (7), did not show any specific binding of $^{125}$I-GRP. Thus, membrane fractions of Swiss 3T3 cells prepared and assayed with solutions containing Mg$^{2+}$ at 5 mM were used to define the kinetic and equilibrium characteristics of $^{125}$I-GRP binding.

Time-course of association and dissociation of $^{125}$I-GP, P

Figure 7A:
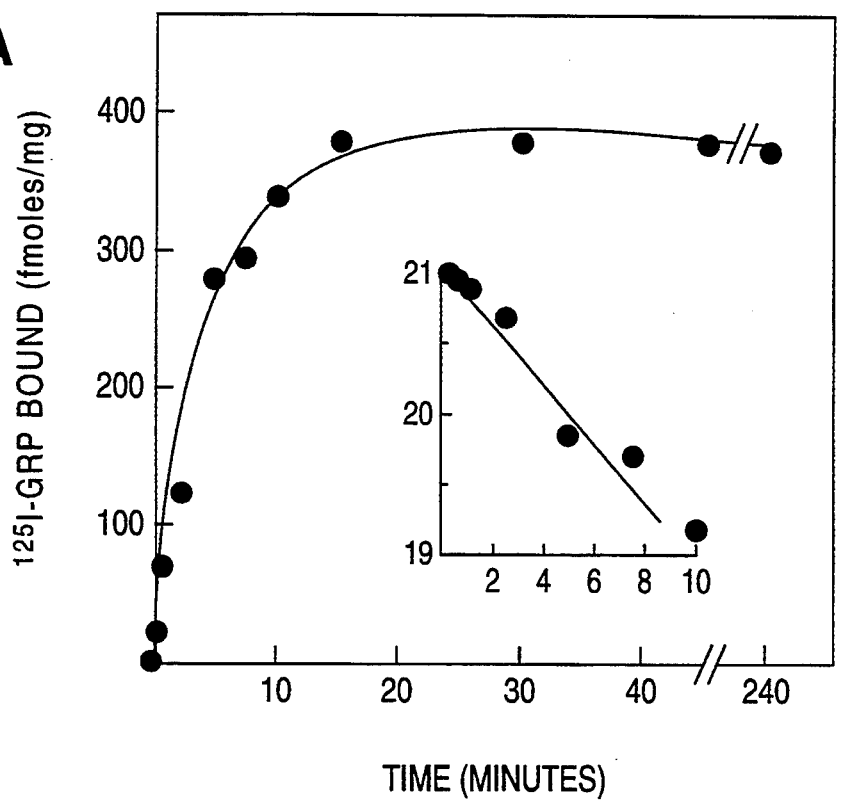

The rate of $^{125}$I-GRP binding to membrane fractions of Swiss 3T3 cells was measured at 15° C. using $^{125}$I-GRP at 0.5 nM (FIG. 7). Under these conditions, specific binding of $^{125}$I-GRP reached 50% of its equilibrium value within 2.5 minutes and maximum binding was achieved after 15 minutes of incubation. At 37° C., maximum binding was attained more rapidly (within 5 minutes). At 15° C. or 37° C., maximum binding remained constant for 4 hours, indicating that there was no detectable degradation of the ligand during this period. The kinetics of $^{125}$I-GRP association to membrane fraction was analyzed as a bimolecular reaction (see Experimental Procedures). The second-order rate constant ($k_1$) obtained from the slope of the line shown in FIG. 7A insert was $0.33 \times 10^9 M^{-1} min^{-1}$.

Figure 7B:
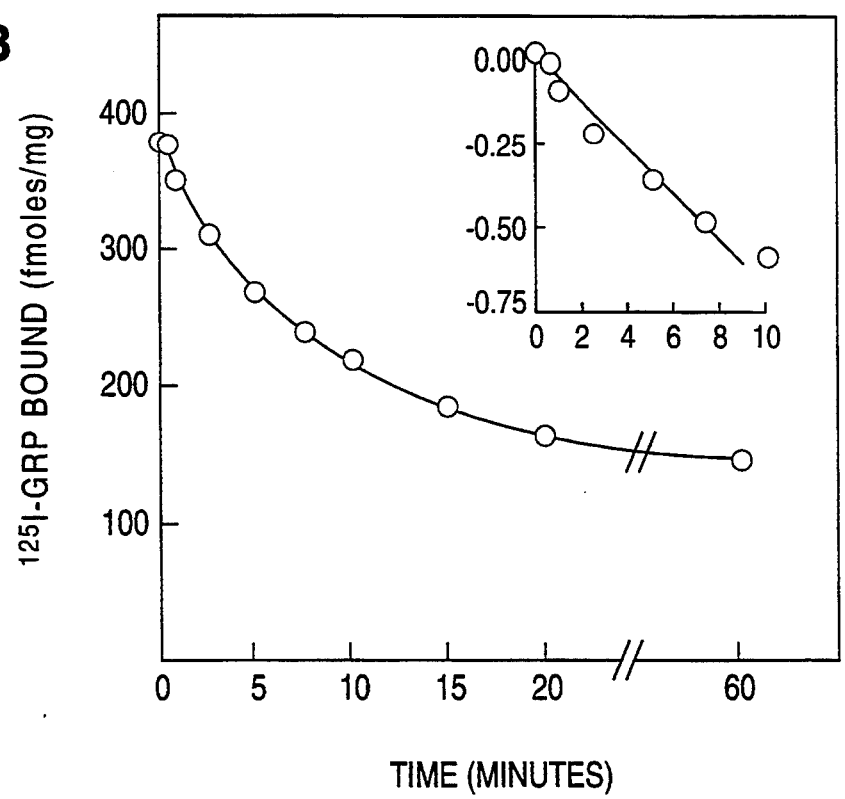

The binding of $^{125}$I-GRP to membrane preparations was reversible. Addition of a 2000-fold excess of unlabelled bombcain to the membrane fractions incubated with $^{125}$I-GRP for 30 minutes, promoted first-order dissociation of the labelled ligand-receptor complex (FIG. 7B). Half-maximal loss of $^{25}$I-GRP binding occurred after 7.5 minutes and the value of $k_2$, the rate constant of dissociation was 0.062 min$^{-1}$. With the values of the rate constant derived from FIG. 7, the equilibrium dissociation constant ($K_d = k_2/k_1$) can be calculated as $1.9 \times 10^{-10}$ M.

Figure 8A:
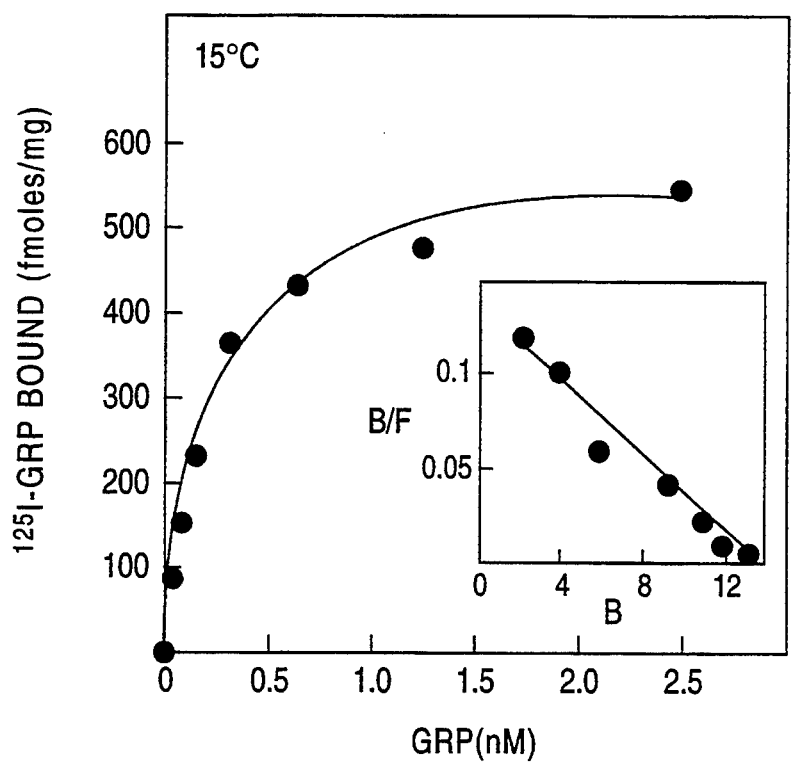
Figure 8B:
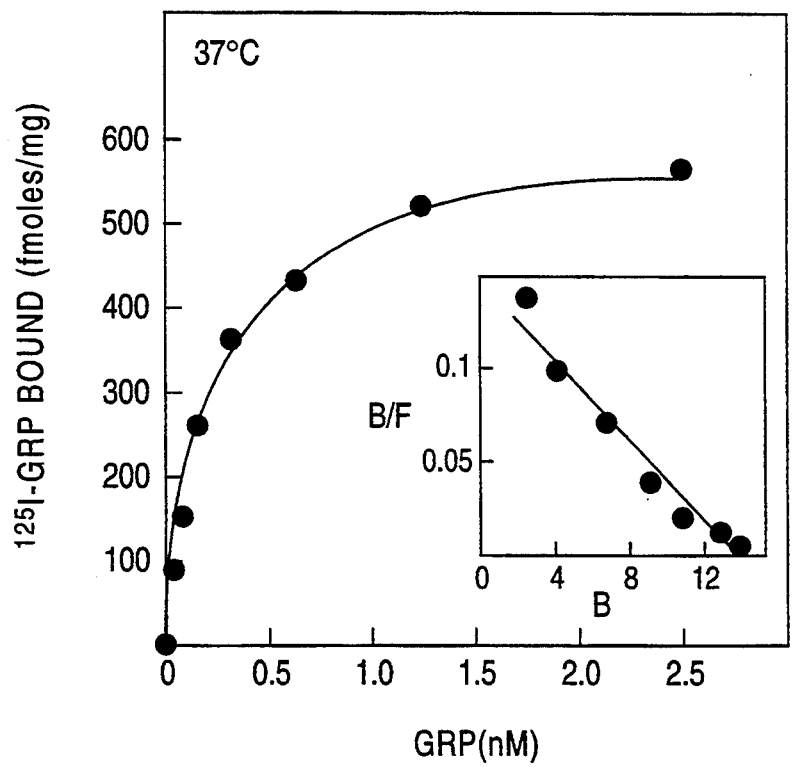

Concentration-depepdence of $^{125}$I-GRP binding to membrane preparations from 3T3 cells Binding of $^{125}$I-GRP to membrane preparations from Swiss 3T3 cells as a function of increasing concentrations of the radiolabelled ligand is shown in FIG. 8. Specific binding of $^{125}$I-GRP measured under equilibrium conditions at 15° C. was saturable while the non-specific GRP binding increased linearly with increasing ligand concentration (not shown). Scatchard analysis (FIG. 8, inset) of these equilibrium binding data indicated the presence of a homogeneous population of high-affinity binding sites of $K_d$-$10^{-10}$ M and a value for the maximal binding capacity (B max) of 550 fmole/mg of cell membrane protein. In 6 independent experiments performed at 15° C. the values of $K_d$ and B max were $2.1 \pm 0.035$ $10-10$ M and $580 \pm 50$ fmole/mg of protein respectively. Similar experiments carried out at 37° C. also showed saturable binding, the presence of a single class of high-affinity sites of $K_d = 2.19 \pm 0.04$ $10^{-10}$ M (n=4 experiments) and maximal binding capacity of $604 \pm 40$ fmole/mg of protein (FIG. 8). These values of $K_d$ are in agreement with the value of $K_d$ calculated on the basis of the rate of constants of association and dissociation derived from the data shown in FIG. 7.

Figure 9:
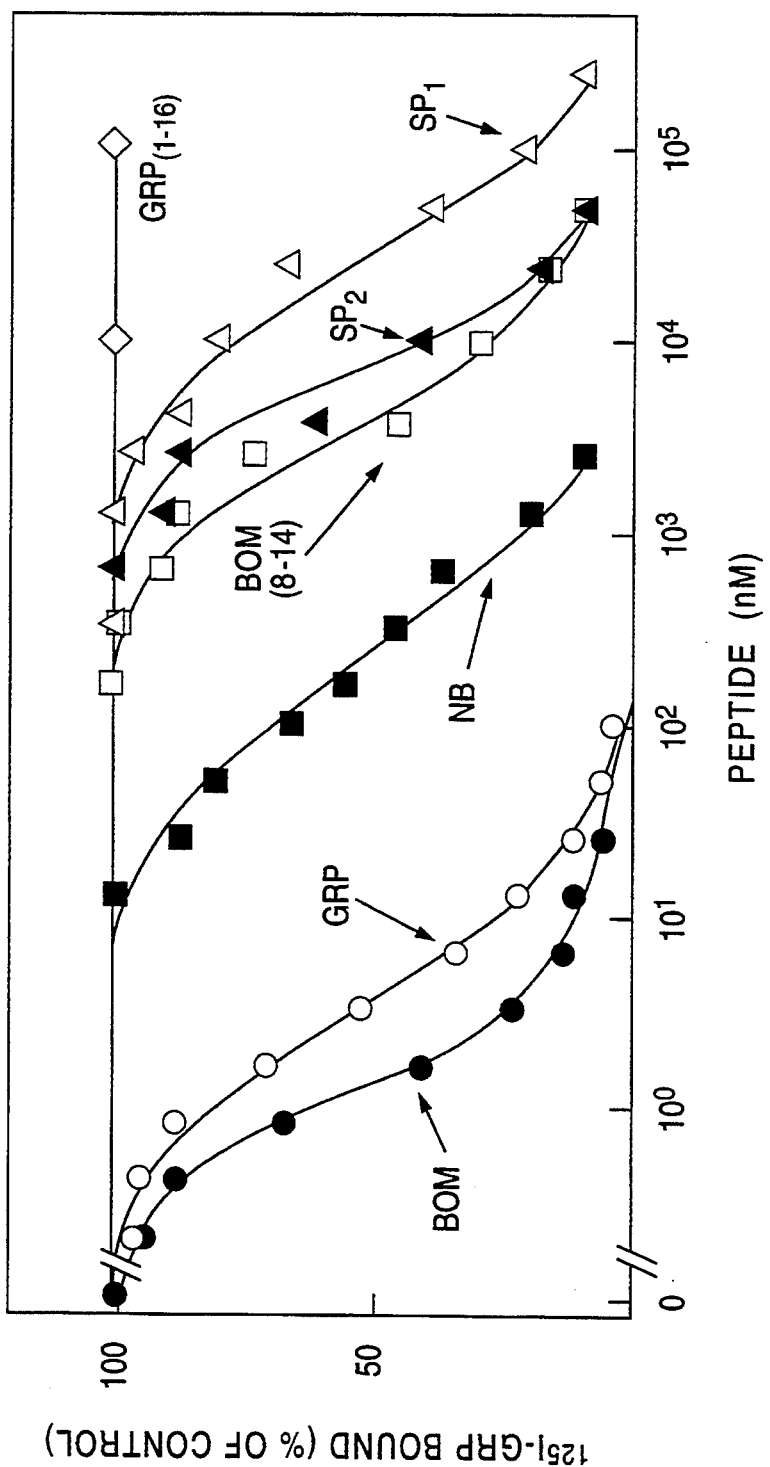

Bombesin agonists and antagonists inhibit $^{125}$I-GRP binding to membrane preparations The ability of a range of peptides structurally related to GRP to inhibit specific $^{125}$I-GRP binding to membrane preparations is shown in FIG. 9. The addition of bombesin, unlabelled GRP, neuromedin B or the (B-14) amino acid fragment of bombcain inhibited specific binding of $^{125}$I-GRP to the membrane preparation in a concentration-dependent manner. Concentrations giving rise to half-maximal inhibition (IC$_{50}$) for bombesin, GRP, neuromedin B and bombesin (8–14) were 1.5, 3.8, 180 and 4000 nM respectively. In contrast, the biologically inactive NH$_2$-terminal fragment of GRP (GRP1-16) did not inhibit binding at concentrations up to 100 µM.

The neuropeptide substance P (SP) neither inhibits the binding of $^{125}$I-GRP to 3T3 cells nor stimulates DNA synthesis in these cells (7,8). However, SP antagonists are potent bombcain antagonists in 3T3 cells (44,45). FIG. 9 also shows the effect of various concentrations of [DArg$^1$,DPro$^2$,DTrp$^{7,9}$, Leu$^{11}$]Sp (8,44) and [DArg$^1$,DPhe$^5$, DTr$^{7,9}$,Leu$^{11}$]SP (45) on the specific binding of $^{125}$I-GRP to membrane preparations of Swiss 3T3 cells. These antagonists decreased binding in a concentration-dependent fashion. The concentrations of [DArg$^1$,DPro$^2$,DTr$^{7,9}$,Leu$^{11}$]SP and [DArg$^1$,DPhe$^5$,DTrp$^{7,9}$,Leu$^{11}$]SP which produced 50% inhibition of binding were 38 µM and 7 µM respectively.

Figure 10:
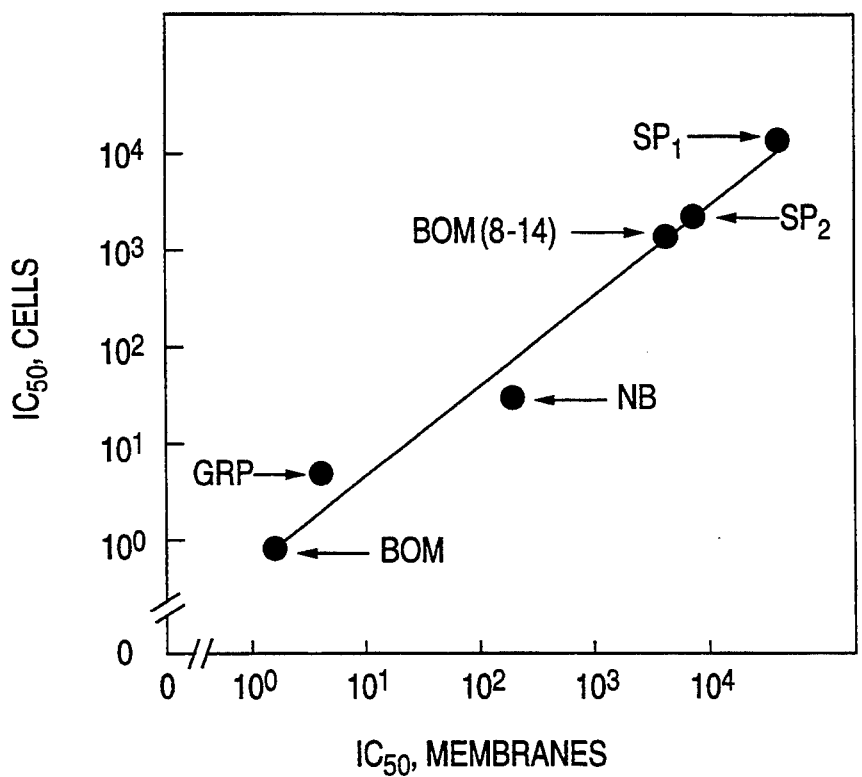
FIGS. 6 to 12 illustrate the results of experiments using the receptor isolated from a $Mg^{++}$stabilised membrane preparation of Swiss 3T3 cells.

The concentrations of agonists and antagonists required to produce 50% inhibition of specific $^{125}$I-GRP binding to membranes (IC$_{50}$) were derived from FIG. 9. The concentrations of these peptides that cause 50% inhibition of $^{125}$I-GRP binding to whole Swiss 3T3 were derived from previously published data (8,45). FIG. 10 shows that the IC$_{50}$ values obtained with membranes correlated extremely well (r=0.98) with the IC$_{50}$ values for binding to intact cells. The striking parallelism between the ability of the peptides to inhibit $^{125}$I-GRP binding both to membrane fractions and to intact cells considerably strengthens our conclusion that the membrane fractions prepared in the presence of Mg$^{2+}$retain the bombesin/GRP binding sites that mediate the mitogenic effects of this family of peptides.

Cross-linking of $^{125}$I-GRP to its receptor in membrane preparations

We have previously identified by chemical cross-linking a surface glycoprotein in intact Swiss 3T3 cells of apparent Mr 75,0000-85,000 which may represent a major component of the receptor for peptides of the bombesin family in these cells (30,31) Similar results have been obtained in other laboratories (32,46). However, because $^{125}$I-GRP became cross-linked to other proteins in whole cells (30–32,46), it was important to identify the component(s) in the membrane fraction that specifically recognizes $^{125}$I-GRP.

Figure 11A:
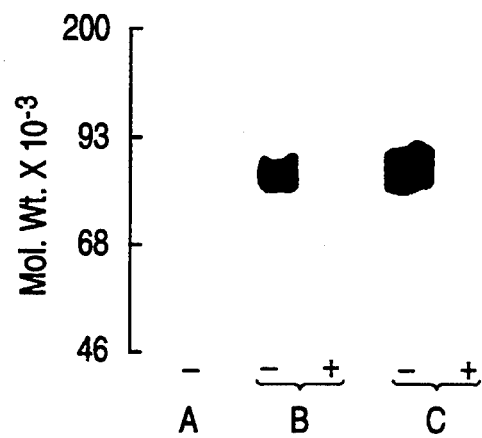
Figure 11C:
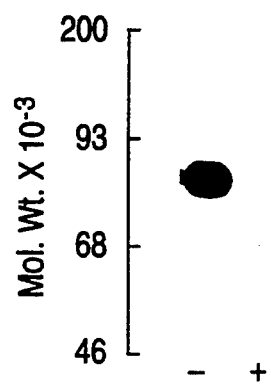
Figure 11B:
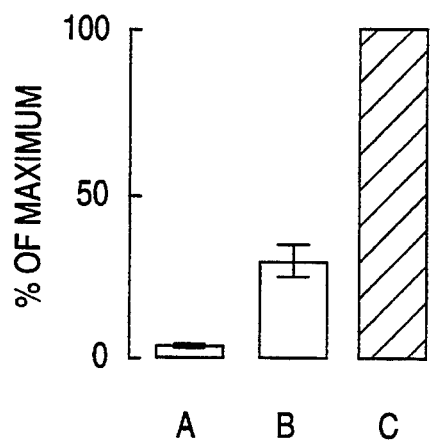

Membrane fractions from Swiss 3T3 cells, prepared in the absence or presence of 5 mM Mg$^{2+}$, were incubated with $^{125}$I-GRP and subsequently treated with the homobifunctional disuccinimidyl cross-linking agent EGS. Analysis by SDS-PAGE followed by autoradiography revealed the presence of a single band migrating with an apparent Mr 75,000–85,000 in membranes prepared in the presence of Mg$^{2+}$ (FIG. 11). The formation of this cross-linked complex was completely abolished by addition of a 1000-fold excess of unlabelled GRP. The Mr 75,000–8.5,000 affinity labelled band was not obtained when the cross-linking reaction was carried out with membrane fractions prepared and assayed in the absence of Mg$^{2+}$. When membranes prepared without ME$^{2+}$ were incubated with $^{125}$I-GRP in the presence of this ion, the labelling of the Mr 75,000–85,000 band was only 31±4% of that observed with membranes prepared and incubated in the presence of ME$^{2+}$ (FIG. 11). Thus, the formation of the Mr 75,000–85,000 cross-linked complex correlated extremely well with the level of specific $^{125}$I-GRP binding in the membrane fractions. Mg$^{2+}$ was essential to preserve both specific binding activity and affinity labelling.

EGS promoted cross-linking of $^{125}$I-GRP to the Mr 75,000–85,000 in concentration dependent manner. Maximum effect was achieved at a concentration of EGS of 4 mM and half maximal at 2.5 mM. The cross-linking agent DSS at 2 mM was as effective as EGS in cross-linking $^{125}$I-GRP to the Mr 75,000–85,000 protein (results not shorn). Affinity labelling of the Mr 75,000–85,000 protein was also prominent vhen using membrane fractions prepared by centrifugation through a sucrose solution (FIG. 11, right).

To assess the specificity with which $^{125}$I-GRP recognizes the Mr 75,000–85,000 protein, membrane fractions were incubated with $^{125}$I-GRP in the absence or presence of various mitogens and neuropeptides. As shown in Table II, the cross linking of $^{125}$I-GRP to membrane fractions of Swiss 3T3 cells was markedly inhibited by other peptides structurally related to GRP, including bombesin, litorin and neuromedin B. In contrast, the amino-terminal fragment of GRP GRP(1–16)) caused no reduction in the level of the Mr 75,000–85,000 protein. Furthermore, none of the other neuropeptides and growth factors tested reduced. the affinity labelling of the Mr 75,000–85,000 band. These results are in accord with the finding that the specific binding of $^{125}$I-GRP to membrane fractions of Swiss 3T3 cells is also not inhibited by these mitogens (Table I).

Figure 12A:
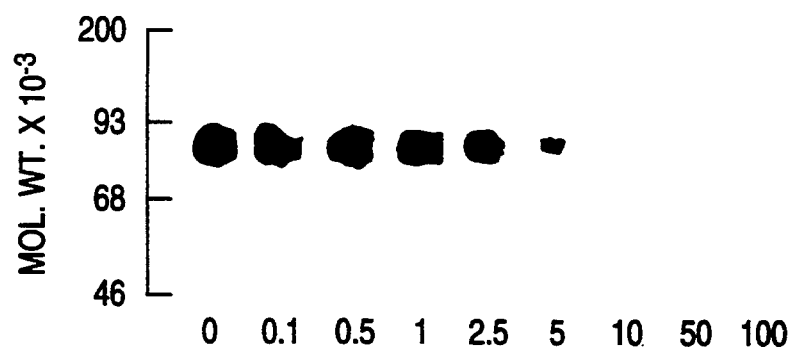
Figure 12B:
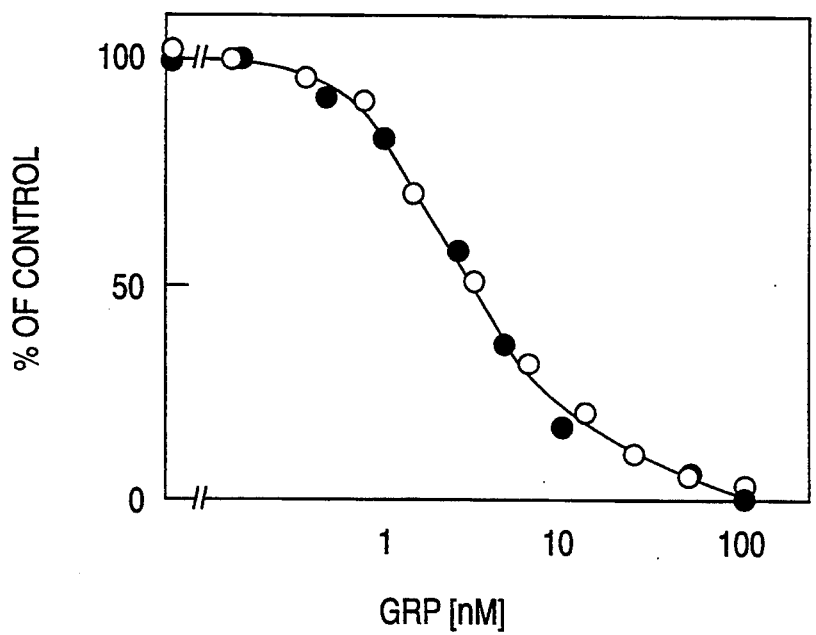

The possibility that the Mr 75,000–85,000 complex is closely related to the receptor for peptides of the bombesin family was substantiated by cross-linking $^{125}$I-GRP to membrane fractions of Swiss 3T3 cells in the presence of different concentrations of unlabelled GRP (FIG. 12, top). Densitometric analysis of the autoradiograms show that the decrease in the level of the Mr 75,000–85,000 band with increasing concentrations of unlabelled GRP closely paralleled the ability of GRP to inhibit the specific binding of $^{125}$I-GRP to membrane preparations (FIG. 12, bottom).

DISCUSSION

The characterization of bombesin receptors is an essential step in the elucidation of the molecular basis of the potent mitogenic response initiated by neuropeptides of the bombesin family in cultures of Swiss 3T3 cells. While binding of $^{125}$I-GRP to whole cells has provided valuable information (8,30,31,45), it has also been shown that $^{125}$I-GRP is rapidly internalized and subsequently degraded by 20. intact Swiss 3T3 cells through a lysosomal pathway (33). These metabolic changes severely complicate the measurements of the kinetic and equilibrium characteristics of the binding reaction at physiological temperatures.[2] Membrane preparations that retain specific binding circumvent these complications.

Several procedures to prepare membranes from cultured cells and tissues (38–43) failed to preserve $^{125}$I-GRP binding activity in membranes derived from 3T3 cells. In the course of these experiments, ve found that addition of ME$^{2+}$ during the preparations of membrane fractions and binding assays resulted in a striking increase of the specific binding of $^{125}$I-GRP. The effect was selective; ME$^{2+}$ could be partially replaced by Mn$^{2+}$though not by Ca$^{2+}$. This effect was not noticed in previous studies using rat brain membranes (42) or membranes from pituitary cells (47) in which bombcain stimulates short-term secretion rather than cell proliferation. In our studies the presence of ME$^{2+}$ during the homogenization of Swiss 3T3 cells was essential to stabilize the $^{125}$I-GRP binding activity. In the present study we have exploited this novel observation to define the kinetic and equilibrium characteristics of the binding reaction and to determine some of the molecular properties of the binding component(s).

Specific binding of $^{125}$I-GRP to membrane preparations of Swiss 3T3 cells was rapid and reversible. Using the rate constants of association (k$_1$) and dissociation (k$_2$) we calculated an apparent equilibrium dissociation (K$_d$) of $1.9 \times 10^{-10}$M. Scatchard analysis of equilibrium binding data gave a K$_d$=$2.1 \times 10^{-10}$. Hence, the kinetically derived equilibrium constant was in excellent agreement with the K$_d$ obtained from equilibrium binding measurements. These K$_d$ values are in reasonable agreement with the apparent K$_d$ ($5-10 \times 10^{-10}$M) measured previously in intact 3T3 cells (8).

The specificity of the binding sites measured in the present study is supported by the following lines of evidence; a) specific binding of $^{125}$I-GRp is not inhibited by a panel of mitogens for Swiss 3T3 cells and by other neuropeptides, b) membranes prepared in the presence of $Mg^{2+}$ from 3T6 cells, which neither bind $^{125}$I-GRP nor respond to this neuropeptide (7,8), do not exhibit any specific binding activity, c) peptides structurally related to GRP containing the highly conserved COOH-terminal heptapeptide of this neuropeptide family including bombesin, litorin, neuromedin B and the 8-14 fragment of bombesin, inhibited specific binding of $^{125}$I-GRP to membrane preparations in a concentration-dependent manner, d) two substance P derivatives that function as bombesin antagonists (8,44,45) also inhibited $^{125}$I-GRP binding to membranes. In fact, the relative potency of various non-radioactive agonists and antagonists to displace $^{125}$I-GRP from membrane preparations correlates extremely yell ($r=0.98$) with the relative abilities of these peptides to inhibit $^{125}$I-GRP binding to intact and quiescent Swiss 3T3 cells (FIG. 10). The relative potency of the bombesin agonists to elicit $Ca^{2+}$-mobilization (19,21), ouabain-sensitive $Rb^+$ uptake (21), protein kinase C mediated phosphorylation of an acidic Mr 80,000 substrate (22,25), inhibition of $^{125}$I-EGF binding (9,22), enhancement of cAMP accumulation (48), induction of c-fos and c-myc expression (29) and stimulation of DNA synthesis in Swiss 3T3 cells (7,8) is the same as their relative abilities to inhibit specific binding of $^{125}$I-GRP to membranes derived from 3T3 cells (FIG. 9). Taken together, these results indicate that the high-affinity binding sites measured in membrane preparations during this study represent the receptor that mediates the mitogenic effects of the peptides of the bombesin family. We have previously identified by chemical cross-linking a cell surface glycoprotein in Swiss 3T3 cells of apparent Mr 75,000-85,000 which may represent a major component of the bombesin receptor (30,31). Studies from other laboratories also observed a similar cross-linked complex though other bands were also noted (32,46). It has also been reported that a Mr 115,000 protein in Swiss 3T3 cells was phosphorylated at tyrosine in response to bombesin (49) and the possibility that the bombesin receptor is associated with this kinase activity was raised. However, bombesin-stimulated tyrosine kinase was not detected by another laboratory (23) and the Mr of the tyrosine phosphorylated band does not coincide with that of the putative receptor identified by affinity cross-linking in whole cells (30-32). In view of these results it was of great interest to determine by chemical cross-linking the component(s) that specifically recognizes $^{125}$I-GRP in these membrane preparations.

In the present study the disuccinimidyl cross-linking agent EGS was used to covalently link $^{125}$I-GRP to an Mr 75,000-85,000 protein of membrane preparations of Swiss 3T3 cells. Affinity labelling of this component was specific, and only observed with membrane fraction prepared in the presence of $Mg^{2+}$. To our knowledge, this is the first time that $^{125}$I-GRP has been cross-linked to a protein binding site in a membrane preparation of target cells or tissues. A salient feature of our results is that the Mr 75,000-85,000 affinity labelled band was the only cross-linked complex detected in the membranes. These findings strongly suggest that the Mr 75,000-85,000 protein identified in this study in membrane preparations and previously in whole 3T3 cells is the receptor or a binding subunit of the bombesin receptor. The availability of-membrane preparations that retain specific bombesin receptors will be useful in the characterization of their molecular and regulatory properties. Moreover, such membrane preparations provide an essential step for attempting the solubilization and purification of this important neuropeptide receptor.

FIGURE LEGENDS

FIG. 6: Dependence on $Mg^{2+}$ of specific binding of $^{125}$I-GRP to the membrane fraction fromm Swiss 3T3 cells.

A. Binding of $^{125}$I-GRP to the membrane fractions from Swiss 3T3 cells prepared and asseyed either in the absence (open bar) or in the presence (hatched bar) of 5 mM $MgCl_2$. The membrane fractions were prepared as described in "Experimental Procedures". Specific binding of $^{125}$I-GRP (0.5 nM) to the membrane fractions (25 μg) was determined as described in "Experimental Procedures". The results represent the mean±SEMn=15, from experiments performed at 15° C. and 37° C.

B. Specific binding of $^{125}$I-GRP as a function of membrane fraction protein. $^{125}$I-GRP (0.5 nM) was incubated at 15° C. for 30 minutes with various concentrations of membranes prepared and assayed either in the absence (open squares) or presence of 5 mM $MgCl_2$ (closed squares). In this experiment total incubation volume was 250 μl to ensure that the availability of free ligand was not limiting. The results represent the mean of 3 separate experiments.

C. Specific binding of $^{125}$I-GRP to Swiss 3T3 membranes is dependent on $MgCl_2$ concentration. The membrane fraction from Swiss 3T3 cells was prepared as described in "Experimental Procedures" except that the $MgCl_2$ concentration was varied as indicated throughout the preparation. Specific binding of $^{125}$I-CRP (0.5 riM) to 25 μg of membranes in the presence of various concentrations of $MgCl_2$ as indicated was determined as described in "Experimental Procedures". Inset. Specific binding of $^{125}$I-GRP (0.5 nM) to membrane fraction aliquots (25 μg) from Swiss 3T3 cells, prepared at the indicated $MgCl_2$ concentration and assayed with 5 mM $MgCl_2$ (o) or prepared in the absence of $MgCl_2$ and assayed at the indicated concentration of $MgCl_2$. Binding in all cases was at 15° C. for 30 minutes. The results are expressed as the mean of triplicate determinations, which varied less than 5% of the mean.

FIG. 7: Kinetics of $^{125}$I-GRP binding to the Swiss 3T3 membrane fraction.

Left panel: Association time course of $^{125}$I-GRP binding to Swiss 3T3 membranes. $^{125}$I-GRP (0.5 nM) was incubated with 25 μg of membrane protein in 100 ul of binding medium at 15° C. for the indicated times. $^{125}$I-GRP specific binding was then determined as described in "Experimental Procedures". Inset: Semilogarithmic plot of the data. Time was plotted on the abscissa and in [(Beg-Bt)/(BoLo-BeqBt)] was plotted on the ordinate. Bo, the initial concentration of free receptors, was estimated from the Scatchard analysis FIG. 8 (left) to be 0.137 nM. Beg the equilibrium concentration of occupied receptors, was taken as 0.095 nM, that obtained after 30 minutes. Lo was the initial ligand concentration (0.5 nM). The slope of the linear regression line through the initial points (0 to 8 minutes) gives the second-order association rate constant $k_1$ according to relationship $k_1 = slope \times (Beq/Beg^2 - BoLo)$.

Right panel: Time course of $^{125}$I-GRP dissociation from Swiss 3T3 membranes. Membranes (25 μg) were incubated with $^{125}$I-GRP (0.5 nM) in 100 μl of binding medium, at 15° C. for 30 minutes. Excess bombesin (1 μM) was then added to each tube, and $^{125}$I-GRP specific binding was determined at the indicated times as described in "Experimental Procedures". Each point represents the average of 3 determinations in one experiment. Inset: Semi-logarithmic plot of the data. Time was plotted on the abscissa and ln(Bt/Beg) was plotted on the ordinate. The slope of the line gave the first order rate constant $k_2$.

FIG. 8: Analysis of binding as a function of $^{125}$I-GRP concentration at 15° C. and 37° C. to the membrane fractions derived from Swiss 3T3 cells.

Membranes (25 μg) in 100 μl of binding medium were incubated in the presence of various concentrations of $^{125}$I-GRP at either 15° C. or 37° C. as indicated. Specific binding was determined after 10 minutes at 37° C. or 30 minutes at 15° C. as described in "Experimental Procedures". Nonspecific binding was measured by the addition of at least 1000 fold excess unlabelled bombcain or 1 μM bombesin for concentrations of $^{125}$I GRP below 1 nM. The insets show Scatchard analysis of the data: bound (B) $^{125}$I-GRP is expressed as fmole/25 μg of membrane protein; F, the free $^{125}$I-GRP concentration, is expressed in pM.

FIG. 9: Effect of various bombesin agonists and antagonists on the specific binding of $^{125}$I-GRP to the membrane fraction prepared from Swiss 3T3 cells.

$^{125}$I-GRP (0.5 nM) and 25 μg of the membrane fraction from Swiss 3T3 cells were incubated in binding medium (100 μl) at 15° C. for 30 minutes in the absence or presence of the following agonists and antagonists at the concentrations indicated, bombesin (●, bom), GRP (o), neuromedin B (■, NB), bombcain 8-14 (□, Bom(-8-14)), GRP 1-16 (◊, GRP), [DArg$^1$,DPhe$^5$,DTrp$^{7,9}$,Leu$^{11}$]substance P (▲, SP2), [DArg$^1$,DPro$^2$,DTrP$^{7,9}$,Leu$^{11}$]substance P (△, SP1). The reactions were terminated and specific binding determined as described in "Experimental Procedures". The results are a composite of two individual experiments and are expressed as a percentage of the control value in each case. The mean control value of specific binding of $^{125}$I-GRP was 290±25 fmole/mg of protein (mean±SEM, n-14).

FIG. 10: The potency of various non-radioactive bombesin agonists and antagonists to inhibit $^{125}$I-GRP binding to membranes derived from Swiss 3T3 cells correlates with the ability of these peptides to inhibit $^{125}$I-GRP bincling to intact Swiss 3T3 cells.

The concentrations (nM) of peptides abbreviated as in FIG. 9 which gave 50% inhibition in the binding of $^{125}$I-GRP to membranes prepared from Swiss 3T3 cells (IC$_{50}$, Membranes), obtained from FIG. 9 were plotted against the concentrations (nM) of the same peptides which gave a 50% inhibition of $^{125}$I-GRP binding to intact Swiss 3T3 cells (IC$_{50}$, Cells), obtained from previously published data (8,45).

FIG. 11: Affinity labelling of a 75,000–85,000 membrane protein with the homobifunctional cross-linking agent EGS.

Left-hand Panel. Dependence on Mg$^{2+}$for specific affinity labelling. Swiss 3T3 membrane fractions were prepared as described in "Experimental Procedures" without MgCl$_2$ (A,B) or with 5 mM MgCl$_2$ (C). Aliguots (150 μg) were incubated in 500 μl of cross-linking medium without MgCl$_2$ (A) or with 5 m MgCl$_2$ (B,C) containing 0.5 nM $^{125}$I-GRP, either in the absence=(—) or presence (+) of 1μM bombesin. Following a 30 minutes incubation at 15° C., the membranes were peleted by centrifugation and chemical cross-linking with EGS (4 mM), in the absence (A) or presence (B,C) of 5 mM MgCl$_2$, was carried out as described in "Experimental Procedures". Representative autoradiograms obtained from SDS-PAGE analysis as described in "Experimental Procedures" are shown in the left hand panel and the bar chart represents the mean±SEM n=4 obtained from scanning densitometry of the autoradiograms. Similar results were obtained following incubations at 37° C. for 10 minutes.

Right-hand Panel. Chemical cross-linking to Swiss 3T3 membranes further purified by centrifugation on a sucrose solution. Cells were harvested and homogenized as described in "Experimental Procedures". The supernatant obtained after the removal of whole cells and nuclei was layered onto solution A containing 45% (w/v) sucrose and centrifuged at 9000 x g for 30 minutes. The plasma membranes were collected from the interface, diluted five-fold with solution A and centrifuged at 30000 x g for 30 minutes. The pellet was resuspended in the same buffer at a concentration of 1 mg/ml. The membranes (75 μg) were then incubated at 37° C. for 10 minutes in 500 μl of cross-linking medium with 0.5 nM $^{125}$I-GRP in the absence (—) or presence (+) of bombsesin (1 μM). Chemical cross-linking at 37° C. using EGS (4 mM) and analysis by SDS-PAGE were carried out as described in "Experimental Procedures". The specific binding measured at 0.5 nM $^{125}$I-GRP of this preparation was 790 fmole/mg and represented a 2 fold increase in specific activity of membranes used in the left-hand panel.

FIG. 12: GRP inhibits the affinity labelled 75,000–85,000 membrane protein in a concentration-dependent manner.

Membrane protein (150 ug) prepared from Swiss 3T3 cells as described in "Experimental Procedures" were incubated in cross-linking medium containing 0.5 nM $^{125}$I-GRP at 37° C. for 10 minutes. Chemical cross-linking using EGS (4 mM) was then carried out as described in "Experimental Procedures". The samples were analysed by SDS-PAGE as described in "Experimental Procedures". The upper panel shows representative autoradiograms. The values shown in the bottom panel are expressed as a percentage of the maximum level obtained from scanning densitometry of autoradiograms (●) and are the mean of two independent experiments. For comparison the dose response of unlabelled GRP inhibition of $^{125}$I-GRP binding to membranes (o) (obtained from FIG. 9) is shown.

TABLE 1

| Binding of $^{125}$I-GRP to Swiss 3T3 membranes is specific | |
|---|---|
| Addition | fmole/mg protein |
| None | 305 ± 9 |
| Bombesin | 7 ± 0.2 |
| GRP(1-27) | 3 ± 0.1 |
| GRP(1-16) | 299 ± 8 |
| Vasopressin | 353 ± 10 |
| Bradykinin | 302 ± 9 |
| VIP | 353 ± 10 |
| Substance P | 305 ± 4 |
| Substance K | 314 ± 5 |
| Somatostatin | 308 ± 8 |
| PDGF | 341 ± 9 |
| FGF | 299 ± 9 |
| EGF | 305 ± 6 |
| Insulin | 332 ± 6 |
| PBt$_2$ | 305 ± 9 | po Membrane fraction protein aliquots (25 μg) from Swiss 3T3 cells were incubated in binding medium containing 0.5 nM $^{125}$I-GRP and the above mitogens at the following concentrations: bombesin and GRP (100 nM); GRP(1-16) vasopressin, bradykinin, VIP, Substance P, Substance K and somatostatin (1μM); PDGF (15 nM); FGF (6 nM); EGF (40 nM). Insulin (1.5 μM); PBt$_2$ (400 nM). Following incubation at 37° C. for 10 minutes specific binding was determined as described in "Experimental Procedures". The results shown are the mean±SEM, n=3. Similar results were obtained in two other independent experiments.

TABLE 2

| Specificity of $^{125}$I-GRP affinity labelling of the $M_r$ 75,000-85,000 protein | |
|---|---|
| Addition | % of maximum |
| None | 100 |
| Bombesin | 5 ± 1 |
| Litorin | 3 ± 1 |
| GRP(1-27) | 4 ± 1 |
| Neuromedin B | 7 ± 2 |
| Bombesin(8-14) | 5 ± 2 |
| GRP(1-16) | 102 ± 3 |
| Vasopressin | 102 ± 1 |
| Bradykinin | 95 ± 3 |
| Substance P | 93 ± 2 |
| PDGF | 104 ± 1 |
| FGF | 101 ± 1 |
| EGF | 108 ± 1 |
| Insulin | 113 ± 3 |
| PBt$_2$ | 111 ± 2 |

Membrane protein aliquots (150 μg) from Swiss 3T3 cells were incubated in cross-linking medium containing 0.5 nM $^{125}$I-GRP and the above reagents at the following concentrations, bombesin, litorin and GRP(1-27) (100 nM); bombcain(8-14) and GRP(1-16) (10 μM), neuromedin B, vasopressin, bradykinin and substance P (1μM); PDGF (15 nM); FGF (6 nM) EGF (40 nM). Insulin (1.5 μM); PBt$_2$ (400 nM). Following incubation at 37° C. for 10 minutes the membranes were pelleted by centrifugation and chemical cross-linking carried out as described in "Experimental Procedures" using 4 mM EGS. The samples were analyzed by SDS-PAGE and scanning densitometry of the autoradiograms as described in "Experimental Procedures". The results shown represent the mean values of three independent experiments expressed as a percentage of the level obtained in the absence of additions.

| Footnote 1: List of Abbreviations | |
|---|---|
| PBS | phosphate buffered saline |
| BSA | bovine serum albumin |
| GRP | gastrin releasing peptide |
| EGS | ethyleneglycolbis(succimidylsuccinate) |
| DSS | disuccinimidyl suberate |
| EGTA | ethylene bis (oxyethylenenitrilo) tetraacetic acid |
| Hepes | 4-(2-hydroxyethyl)-1-piperazineethanesulfonic acid |
| SDS-PAGE | sodium dodecyl sulfate-polyacrylamide gel electrophoresis |
| VIP | vasoactive intestinal peptide |
| PDGF | platelet-derived growth factor |
| FGF | fibroblast growth factor |
| EGF | epidermal growth factor |
| PBt$_2$ | phorbol 12,13-dibutyrate |

Footnote 2: LiEand internalization and degradation are markedly decreased at 4° C. (33). However, binding of $^{125}$I-GRP to intact cells proceeds very slowly at 4° C. It is difficult to achieve precise equilibrium binding even after many hours of incubation at this unphysiological temperature.

References

1. Zachary, I., Woll, P.J. and Rozengurt, E. (1987)Dev. Biol. 124, 295-308.
2. Anastasi, A., Erpsamer, V. and Bucci, M. (1971) Experientia 27, 166-167.
3. McDonald, T.J., Jornvall, H., Nilsson, G., Vagne, M., Ghatei, M., Bloom, S.R. and Mutt, V. (1979) Biochem. Biophys. Res. Commun. 90, 227-233.
4. Minamino, N., Kangawa, K. and Matsuo, H. (1983) Biochem. Biophys. Res. Commun. 114, 541-548.
5. Minamino, N., Kangawa, K. and Matsuo, H. (1984) Biochem. Biophys. Res. Commun. 119, 14-20.
6. Minamino, N., Sudoh, T., Kangawa, K. and Matsuo, H. (1985) Biochem. Biophys. Res. Commun. 130, 685-691.
7. Rozengurt, E. and Sinnett-Smith, J. (1983) Proc. Natl. Acad. Sci. USA. 80, 2936-2940.
8. Zachary, I. and Rozengurt, E. (1985) Proc. Natl. Acad. Sci. USA. 82, 7616-7620.
9. Zachary, I. and Rozengurt, E. (1985)Cancer Surv. 4, 729-765.
10. Moody, T.W., Pert, C.B., Gazdar, A.F., Carney, D.N. and Minna, J.D. (1981)Science 214, 1246-1248.
11. Wood, S.M., Wood, J.R., Ghatei, M.A., Lee, Y.C., O'Shaughnessy, D, Bloom, S.R. (1981) J. Clin. Endocrin. Metabol. 53, 1310-1312.
12. Erisman, M.D., Linnoila, R.I., Bernandez, O, Diaugustine R.P. and Lazarus, L.H. (1982) Proc. Natl. Acad. Sci. USA. 79, 2379-2383.
13. Cuttitta, F., Carney, D.N., Mulshine, J., Moody, T.W., Fedorko, J., Fischler, A. and Minna, J.D. (1985) Nature 316, 823-826.
14. Carney, D.N., Cuttitta, F., Moody, T.W. and Minna, J.D. (1987) Cancer Res. 47,821-825.
15. Woll, P.J. and Rozengurt, E. (1988) Br. J. Cancer 57, 579-586.
16. Rozengurt, E. (1986) Science 234, 161-166.
17. Heslop, J.P., Blakeicy, D.M., Brovn, K.D., Irvine, R.F. and Berridge, M.j. (1986) Cell 47,703-709.
18. Takuwa, N., Takuwa, Y., Bollag, W.E., and Rasmussen, H. (1987) J. Biol. Chem. 262, 182-188.
19. Lopez-Rivas, A., Mendoza, S.A., Nanberg, E., Sinherr-Smith, J. and Rozengurt, E. (1987) Proc. Natl. Acad. Sci. USA. 84, 5768-5772.
20. Nanberg, E. and Rozengurt, E. (1988) EMBO J. 7, 2741-2745.
21. Mendoza, S.M., Schneider, J.A., Lopez-Rivas, A., Sinnett-Smith, J.W. and Rozengurt, E. (1986) J. Cell Biol. 102, 2223-2233.
22. Zachary, I., Sinnett-Smith, J.W. and Rozengurt, E. (1986) J. Cell Biol. 102, 2211-2222.
23. Isacke, C.M., Meisenhelder, J., Brown, K.D., Gould, K.L., Gould, S.J. and Hunter, T. (1986) EMBO J. 5, 2889-2898.
24. Rodriguez-Pena, A., Zachary, I. and Rozengurt, E. (1986) Biochem. Biophys. Res. Commun. 140, 379-385.
25. Erusalimsky, J., Friedberg, I. and Rozengurt, E. (1988) J. Biol. Chem. (in press).
26. Brown, K.D., Blay, J., Irvine, R.F., Heslop, J.P. and Betridge, M.J. (1984) Blochem. Biophys. Res. Commun. 123, 377-384.
27. Letterio, J.J., Coughlin, S.R. and Williams, L.T. (1986) Science 234, 1117-1119.
28. Palumbo, A.P., Rossino, P. and Commoglio, P.M. (1986) Exp. Cell Res. 167, 276-280.

29. Rozengurt, E., and Sinnett-Smith, J.W. (1987) J. Cell Physiol. 131, 218–225.

30. Bravo, R., Macdonald-Bravo, H., Muller, R., Hubsch, D. and Almendral, J.M. (1987) Exp. Cell Res. 170, 103–109.

30. Zachary, I. and Rozengurt, E. (1987) J. Biol. Chem. 262, 3947–3950.

31. Sinnett-Smith, J., Zachary, I. and Rozengurt, E. (1988) J. Cell. Biochem. (in press).

32. Kris, R.M., Hazan, R., Viilines, J., Moody, T.W. and Schlessinger, J. (1987) J. Biol. Chem. 262, 11215–11220.

33. Zachary, I. and Rozengurt, E. (1987) EMBO J. 6, 2233–2239.

34. Todaro, G.J. and Green, H. (1963) J. Cell Biol. 17, 299–313.

35. Maelicke, A., Fulpius, W., Klett, R.P. and Reich, E. (1977) J. Biol. Chem. 252, 4811–4830.

36. Dunphy, W.G., Kochenburger, R.J., Castagna, M. and Blumberg, P.M. (1981) Cancer Res. 41, 2640–2647.

37. Laemmli, U.K. (1970) Nature 227, 680–685.

38. Thom, D., Powell, A.J., Lloyd, C.W. and Rees, D.A. (1977) Biochem. J. 168, 187–194.

39. Harshman, S. and Conlin J.G. (1978) Analytical Biochem. 90, 98–106.

40. Motand, J.N. and Kent, C. (1986) Analytical Biochem. 159, 157–162.

41. Fanget, B.O. and Sporn, M.B. (1986) Analytical Biochem. 156, 444–453.

42. Moody, T.W., Pert, C.B., Rivier, J., and Brown, M.R. (1978) Proc. Natl. Acad. Sci. USA. 75, 5372–5376.

43. Scemama, J.L., Zahidi, A., Fourmy, D., Fagot-Revurat, P., Vaysse, N., Pradayrol, L. and Ribet, A. (1986) Regul. Peptides 13, 125–132.

44. Zachary, I. and Kozengurt, E. (1986) Biochem. Biophys. Res. Commun. 137, 135–141.

45. Woll, P.3. and Rozengurt, E. (1988) Proc. Natl. Acad. Sci. USA. 85, 1859–1863.

46. Brown, K.D., Laurie, M.S., Littlewood, C.J., Blakeley, D.M. and Corps, A.N. (1988) Biochem. J. 252, 227–235.

47. Fischer, J.B. and Schonbrumm, A. (1988) J. Biol. Chem. 263, 2808–2816.

48. Millar, J. and Rozengurt, E. (1988) J. Cell. Physiol. 137, 214–222.

49. Cirillo, D.M., Gaudino, G., Naldini, L. and Comoglio, P.M. (1986) Mol. Cell. Biol. 6, 4641–4649.

We claim:

1. A method of retarding or reducing the growth of small cell lung cancer by administering to a host in need of such treatment an amount of antagonist G effective to retard or reduce said growth.

* * * * *